US007264817B1

(12) United States Patent
Berman et al.

(10) Patent No.: US 7,264,817 B1
(45) Date of Patent: *Sep. 4, 2007

(54) IMMUNOGENIC COMPOSITION BASED ON A TRUNCATED DERIVATIVE OF A MEMBRANE BOUND PROTEIN AND PROCESS FOR MAKING IT

(75) Inventors: Phillip W. Berman, San Francisco, CA (US); Laurence A. Lasky, San Francisco, CA (US)

(73) Assignee: Genentech, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/459,141

(22) Filed: Jun. 2, 1995

Related U.S. Application Data

(63) Continuation of application No. 08/357,084, filed on Dec. 15, 1994, now Pat. No. 5,851,533, which is a continuation of application No. 08/171,858, filed on Dec. 21, 1993, now abandoned, which is a continuation of application No. 07/814,243, filed on Dec. 23, 1991, now abandoned, which is a continuation of application No. 07/695,585, filed on May 3, 1991, now abandoned, which is a continuation of application No. 06/878,087, filed on Jun. 24, 1986, now abandoned, which is a continuation of application No. 06/588,170, filed on Mar. 9, 1984, now abandoned, which is a continuation of application No. 06/547,551, filed on Oct. 31, 1983, now abandoned, which is a continuation of application No. 06/527,917, filed on Aug. 30, 1983, now abandoned.

(51) Int. Cl.
*A61K 39/00* (2006.01)
*A61K 39/245* (2006.01)
*A01N 63/00* (2006.01)
*A01N 65/00* (2006.01)
*C12N 15/09* (2006.01)

(52) U.S. Cl. .............................. 424/229.1; 424/231.1; 424/93.1; 435/69.3

(58) Field of Classification Search ............ 424/229.1, 424/231.1, 93.1; 435/69.3
See application file for complete search history.

(56) References Cited

U.S. PATENT DOCUMENTS

| | | | |
|---|---|---|---|
| 4,317,811 A | 3/1982 | Bertland et al. | 424/89 |
| 4,374,127 A | 2/1983 | Larson et al. | 424/89 |
| 4,442,205 A | 4/1984 | Hamer et al. | 435/68 |
| 4,593,002 A | 6/1986 | Dulbecco | 435/172.3 |
| 4,618,578 A | 10/1986 | Burke et al. | 435/68 |
| 4,818,694 A | 4/1989 | Watson et al. | 435/68 |
| 4,855,224 A | 8/1989 | Berman et al. | 435/68 |
| 4,891,315 A | 1/1990 | Watson et al. | 435/69.3 |
| 5,314,808 A | 5/1994 | Tiollais et al. | 435/69.3 |

FOREIGN PATENT DOCUMENTS

| | | |
|---|---|---|
| AU | 1745283 | 2/1984 |
| EP | 0001365 | 4/1979 |
| EP | 0101655 | 2/1984 |
| EP | 0133063 | 2/1985 |
| EP | 0168662 | 1/1986 |
| EP | 0170169 | 2/1986 |
| EP | 0243155 | 10/1987 |
| GB | 2105344 | 3/1983 |
| WO | 8302897 | 9/1983 |
| WO | 8504587 | 10/1985 |

OTHER PUBLICATIONS

Berman, et al, 1988, "Expression of Membrane- . . . " J. Virology 62(9): 3135-3142.*
Rose, et al, 1982, "Expression From Cloned cDNA of . . . " Cell 30 : 753-762.*
Watson, et al, 1982, "Herpes Simplex Virus . . . " Science 218: 381-384.*
Chan, 1983, "Protective Immunization of Mice With . . . " Immunol. 49: 343-352.*
Kantman, et al, 1982, "Construction of a Modular Dihydrofolate . . . " Molec. & Cell Biol. 2(11): 1304-1319.*
Mester et al.; The Mouse and understanding immunity . . . ; Rev. of Inf. Dis.; 13 (supp. 11); S935-S945, 1991.*
Paul Fundamental Immunology, Raven Press, New York, NY; 1993; 3rd Edition, p. 251.*
Yang et al. Improved elicitation of neutralizing antibodies against primary human immunodeficiency viruses by soluble stabilized envelope glycoprotein trimers. Journal of Virology (2001) vol. 75, pp. 1165-1171.*
Dundarov et al. Immunotherapy with inactivated polyvalent herpes vaccines. Development Biolgical Standard. 1982;52:351-8.*
Watson et al., "Herpes Simplex Virus Type-1Glycoprotein D Gene: Nucleotide Sequence and Expression in *Escherichia coli"* *Science*, 218:381-384 (Oct. 22, 1982).
Rose et al., "Expression from Cloned cDNA of Cell-Surface Secreted Forms of the Glycoprotein of Vesicular Stomatitis Virus in Eucaryotic Cells" *Cells*, 30:753-762 (Oct. 1982).
Kaufman et al., "Construction of a Modular Dihydrofolate Reductase cDNA Gene: Analysis of Signals Utilized for Efficient Expression," *Molecular and Cellular Biology*, 3(11):1304-1319 (1982).
Chan, "Protective Immunization of Mice with Specific HSV-1 Glycoproteins," *Immunology*, 49:343-352 (1983).
Dreesman et al., "Antibody to Hepatitis B Surface Antigen After a Single Inoculation of Uncoupled Synthetic HbsAg Peptides," *Nature*, 295:158-160 (1982).

(Continued)

*Primary Examiner*—Bruce R. Campbell
*Assistant Examiner*—Nicole Kinsey
(74) *Attorney, Agent, or Firm*—Beyer Weaver LLP; Emily M. Haliday

(57) ABSTRACT

Disclosed is an invention related to the preparation and use of vaccines against pathogenic organisms, such as herpes virus. The vaccines hereof are based upon the use of truncated, membrane-free derivatives of a membrane-bound polypeptide from the pathogen. These polypeptides when incorporated into a vaccine composition afford protection against pathogenic challenge after administration.

31 Claims, 28 Drawing Sheets

OTHER PUBLICATIONS

Middleton et al, "Expression of Cloned Herpesvirus Genes: Detection of Nuclear Antigens from Herpes Simplex Virus Type 2 Inverted Repeat Regions in Transfected Mouse Cells," *Journal of Virology*, 43(3):1091-1101 (Sep. 1982).

Lee et al., "Expression of Herpes Simplex Virus Glycoprotein C From a DNA Fragment Inserted into the Thymidine Kinase Gene of this Virus," *PNAS, USA*, 79:6612-6616 (Nov. 1982).

Zoler et al., "Scientists Engineer Proteins for Cellular Export," *Bio/Technology* 146-147 (Apr. 1983).

Spear, P.G., "Cell Membranes and Viral Envelopes," *Herpes Viruses*, 2:709-150 (1980).

Balachandran et al., "Protection Against Lethal Challenge of BALB/c Mice by Passive Transfer of Monoclonal Antibodies to Five Glycoproteins of Herpes Simplex Virus Type 2," *Infect. Immun.*, 37:1132-1137 (1982).

Dix et al., "Use of Monoclonal Antibody Directed Against Herpes Simplex Virus Glycoproteins to Protect Mice Against Acute Virus-Induced Neurological Disease," *Infect. Immun.*, 34:192-199 (1982).

Gething et al., "Molecular and Chemical Basis of Virus Virulence and Immunology," *Modern Approaches to Vaccines*, (pub. Cold Spring Harbor Laboratories) Proceedings of Meetings at Cold Spring Harbor: 262-268.

Alt et al, "Synthesis of Secreted and Membrane-Bound Immunoglobin Mu Heavy Chains is Directed by mRNAs that Differ at Their 3' Ends," *Cell*, 20:293-301 (1980).

Early et al., "Two mRNAs Can Be Produced From a Single Immunoglobulin u Gene by Alternative RNA Processing Pathways," *Cell*, 20:313-319 (1980).

Cheng et al., "Structure of Gene for Membrane and Secreted Murine IgD Heavy Chains," *Nature*, 296:410-415 (1982).

Rogers et al., "Gene Segments Encoding Transmembrane Carboxyl Termini of Immunoglobulin Chains," *Cell*, 26:19-27 (1981).

Mertz et al., "Double-Blind, Placebo-Controlled Trial of a Herpes Simplex Virus Type 2 Glycoprotein Vaccine in Persons at High Risk for Genital Herpes Infection," *Journal of Infectious Diseases*, 161:653-660 (1989).

Schrier et al., "Type-Specific Delayed Hypersensitivity and Protective Immunity Induced by Isolated Herpes Simplex Virus Glycoprotein," *J. Immunol.*, 130(3):1413-1418 (Mar. 1983).

Wiley et al., Structural Identification of the Antibody-Binding Sites of Hong Kong Influenza Haemagglutinin and Their Involvement in Antigenic Variation,: *Nature*, 289:373-378 (1981).

Gething et al., "Cell-Surface Expression of Influenza Haemagglutinin from a Cloned DNA Copy of the RNA Gene," *Nature*, 293:620-625 (1981).

Lusky et al., "Inhibition of SV40 Replication in Simian Cells by Specific pBR322 DNA Sequences," *Nature*, 293:79-81 (1981).

Lasky et al., "Protection of Mice From Lethal Herpes Simplex Virus Infection by Vaccination with a Secreted Form of Cloned Glycoprotein D," *Bio/Technology*, (Jun. 1984).

Cohen et al., "Localization and Synthesis of an Antigenic Determinant of Herpes Simplex Virus Glycoprotein D That Stimulates the Production of Neutralizing Antibody," *J. Virol.*, 49:102-108 (1984).

Dietzschold et al., "Synthesis of an Antigeic Determinant of the HSV gD That Stimulates the Induction of Virus-Neutralizing Antibodies and Confers Protection Against a Lethal Challenge of HSV," 145-149.

Eisenberg et al., "Comparative Structural Analysis of Glycoprotein gD of Herpes Simplex Virus Types 1 and 2," *J. Virol.*, 35:428-434 (1980).

Webster's Ninth New Collegiate Dictionary (1983) p. 1301.

The American Heritage Dictionary, Second college Edition, (1991) p. 384.

Bay Area Bioscience Centre "Northern California's Bioscience Legacy" 1-33 (1991).

Hitzeman et al., "Expression of Hepatitis B Virus Surface Antigen in Yeast," *NAR 11*, (9), 2745 (1983).

Wilson et al., "Structure of the Haemagglutinin Membrane Glycoprotein of Influenza Virus at 3 Å Resolution," *Nature 289*, 366 (1981).

Kleid et al., "Cloned Viral Protein Vaccine for Foot-and-Mouth Disease: Responses in Cattle and Swine," *Science 214*, 1125 (1981).

Rose et al., "Conditional Expression of the Vesicular Stomatitis Virus Glycoprotein Gene in *Escherichia coli*," *PNAS USA 78* (11) (1981).

Brand et al., "Crystalline Antigen From the Influenza Virus Envelope," *Nature New Biology 238*, 145.

* cited by examiner

Fig. 1A (Part 1)

Fig. 1A (Part 2)

```
                  *         *         *         *         *         *         *
HSV2 gD Gene   76 AAATACGGCCTTAGCAGACCACCCCTCGCTTAAGATGGCCGATCCCAATCGATTTCGCGGGAAGAACCTTTCCGGTTTG
HSV1 gD Gene      AAATATGGCCTTGGGCGGATGGCCGATGCCTCTCAAGATGGCCGACCCCAATCGCTTTCGCGGCAAGGACCTTCCGGTCCTG
HSV2 gD Protein 26 LysTyrAlaLeuAlaAsp ProSerLeuLysMetAlaAsp ProAsnArgPheArgGly LysAsnLeuProValLeu
HSV1 gD Protein    LysTyrAlaLeuAlaAsp AlaSerLeuLysMetAlaAsp ProAsnArgPheArgGly LysAspLeuProValLeu

*         *         *         *   ***   *         *         *
HSV2 gD Gene  151 GACCAGCTGACCGACCGACCCCCCCCGGGGGTGAAGCGTGTTTACCACATTCAGCAGCCTGAGGACCCGGTTCCAGCCC
HSV1 gD Gene      GACCAGCTGACCGACCGACCCCCTCCGGGGGGTCCGCGTGTCCGCGTGTACCACATCCAGGCGGCCTACCGAACCCGGTTCCAGCCC
HSV2 gD Protein 51 AspGlnLeuThrAspArgProProProGlyVal LysArgValTyrHisIleGlnProSer LeuGluAsp ProPheGlnPro
HSV1 gD Protein    AspGlnLeuThrAspArgProProProGlyVal ArgArgValTyrHisIleGlnAlaGlyLeu ProAsn ProPheGlnPro
                                                                                         Asp

*   *     *   ***   *         *         *         *         *
HSV2 gD Gene  226 CCCAGCATCCCGATCACTGTGTACTACGCGGTGCTGGAACGTGCCTGCCGCAGCGTGCTCCTCCTACATGCCCCATCG
HSV1 gD Gene      CCCAGCCTCCCGATCACGGTGTTACCGCGGTG---GAGCGGGAGGTGCTGCGCGCAGCGTGCTGCTCCTCTAAACGCACGTCG
HSV2 gD Protein 76 ProSerIle ProIleThrValTyr TyrAlaValLeu  GluArg AlaCysArgSerValLeuLeu HisAlaProSer
HSV1 gD Protein    ProSerLeu ProIleThrValTyr AlaValLeu    GluArg GluValLeuArgAlaCysArgSerValLeuLeu AsnAlaProSer

*         *         *   *     *         *         *         *
HSV2 gD Gene  301 GAGGCCCCCCAGAGTCGTGCGCGGGGATTGTCCGCGGGGGCCTTCGGACGAGGACGTTCGGACGAAGACGTACAACACCACCAACCTGACCATGCGCCTGCTT
HSV1 gD Gene      GAGGCCCCCCCAGAGTTGTCCGCGGGGGCCCTCCGAAGACGTTCGGACGAAGACGTCCGGAAACACCCTACAACCCTACAACCTGACCATCGCCATCGCTTGGTTT
HSV2 gD Protein 101 GluAlaProGlnIleValArgGlyAlaSer AspSerGluAspVal ArgLys HisThr TyrAsnLeu IleAlaTrp Tyr
HSV1 gD Protein    GluAlaProGlnIleValArgGlyAlaSer AspSerGluAspVal ArgLys GlnPro TyrAsnLeu IleAlaTrp Phe

*         *         *         *         *         *         *
HSV2 gD Gene  376 CGCATGGGAGACAATTGCGCCTGTCGCTGCTATCCCATCACGGTTATGGAATACACCGAGTGCCCCTACAACAAGTCGTTGGGG
HSV1 gD Gene      CGGATGGGAGGAGCAACTGCGCAATCGTGCAACTGTCGTGCTACCCCATCATGGAGTACGTCATGGAGTACACCGAGTGCGAATGCTCCACACAAGTCTCTGGGG
HSV2 gD Protein 126 ArgMetGly AspAsnCys AlaCys ArgCysTyrProIleThrValMetGluTyrThrGlu Cys ProTyr LeuGly
HSV1 gD Protein    ArgMetGly GlyAsnCys AlaIle ValCysAlaIleProIleMetGluTyrValMetGluTyrThrGlu Cys Ser LeuGly
```

Fig. 1A (Part 3)

```
                  *               *               *               *               *
451  HSV2 gD Gene     GTCTGCCCCATCCGAACGCAGCCCCGCTGGAGCTACTATGACAGCTTTAGCGCCGTCAGCGAGGATAACCTGGGA
     HSV1 gD Gene     GCCTGTCCCATCCGAACGCAGCCCCGCTGGAGCTACTATGACAGCTTCAGCGCCGTCAGCGAGGATAACCTGGGG
151  HSV2 gD Protein       Val CysProIleArgThrGlnProArgTrpSerTyrTyrAspSerPheSerAlaValSerGluAspAsnLeuGly
     HSV1 gD Protein       Ala CysProIleArgThrGlnProArgTrpAsnTyrTyrAspSerPheSerAla

Fig. 1B (Part 1)

```
                                    *                 *                 *                 *                 *
HSV2 gD Gene     826  ACCCTGCTGCCGCCGGAGCTGTCCGACACCACCACCAACGCCACCCGAACTCGTTCCGGAAGACCCCGAGGAC
HSV1 gD Gene          ACCCTGCTGCCGCCGGAGCTGTCCGACACCACCACCAACGCCACCCGAACTCGTTCCGGAAGACCCCGAGGAT
HSV2 gD Protein  276  ThrLeuLeuProProGluLeuSerAspThrThrThrAsnAlaThrGlnProGluLeuValProGluAspProGluAsp
HSV1 gD Protein       ThrLeuLeuProProGluLeuSerAspThrThrThrAsnAlaThrGlnProGlu

Fig. 1B (Part 2)

```
                                                             *        **                          *****  *  **
HSV2 gD Gene          1126  CGTCTCCCCCACATCCGGGATGACGACGCGCCCCCCTCGCACCAGCCATTGTTTACTAGAGGAGTTTCCCCGCT
HSV1 gD Gene           376  CGCCTCCCCCACATCCGGGAAGACGACGACCAGCCGTCCTCCGCACCAGCCCTTGTTTTACTAGA-----TACCCC---
HSV2 gD Protein             ArgLeuProHisIleArgAspAspAla ProSerHisGlnProLeuPheTyrSTOP
HSV1 gD Protein             ArgLeuProHisIleArgAspAspGlu AspAspGln ProSerSerHisGlnProLeuPheTyrSTOP

* ********   *    ****    **        *   * ********                      *                     "TATA3"
HSV2 gD Gene                CCCGTGTACCTCTGAGGCCC-GTGTGGA--GGGTGGCTGGGGTATTTAGGGTGGGACTTGGACTCCGCATAAAGG
HSV1 gD Gene                CCCTTAATGGG-TGCGGGGGGTCAGGTCTGCGGGGTTG------GGATGGGAACCTTAACTCCATATAAAGG

*     *           ***      *   *    *   *     *         *  **    *  *   ***    **********
HSV2 gD Gene                AGTCTCGAAGGAGGAGGGAAACTAGGACAGTTCATAGGCCGGGAGCGTGGGGCGCGCCGTGTCCCGACGATTAG
HSV1 gD Gene                AGTCTGGAAGGGGGGAAGGGGGAAAGGGCGGACAGTCGATAAGTCGGTAGCGGGGACGCGCCACC---TGTTCC------G

**    *       ****       *       *     *
HSV2 gD Gene                CCAGCCGCGCCCACAGCCACCTC--GACCCGGTCCGATCCGCGGTATGCCCGGCCGCTCGCTGCAGGGCCTGGCG
HSV1 gD Gene                CCTGTCGCACCCACCACAGCTTTTTCGCGAACCG-TCCCGTTTT
HSV2 Open Reading                                                          MetProGlyArgSerLeuGlnGlyLeuAla
       Frame HSV2 gD Gene                ATCCTGGGCCTGTGGGTCTGCGCCACCGGCCTGGTCCGT
HSV2 Open Reading           IleLeuGlyLeuTrpValCysAlaThrGlyLeuValArg
       Frame
```

Fig. 4.
A
B
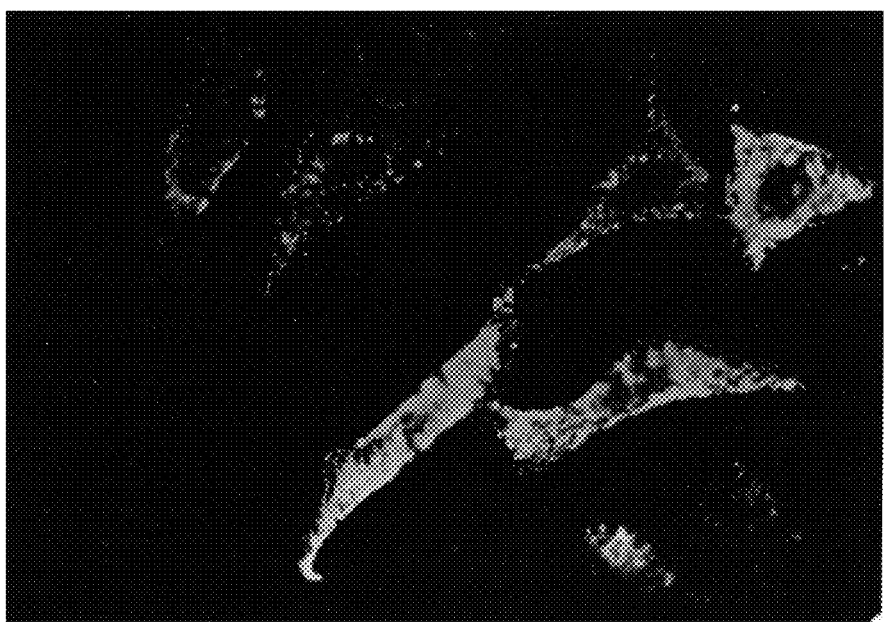

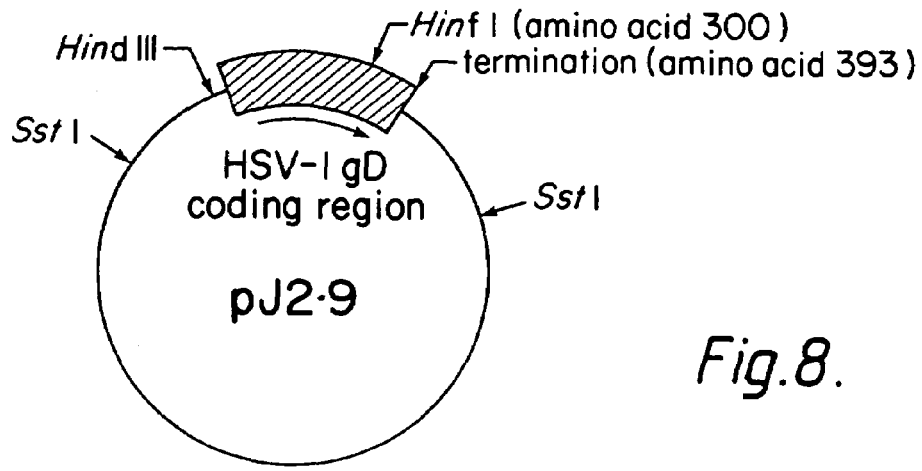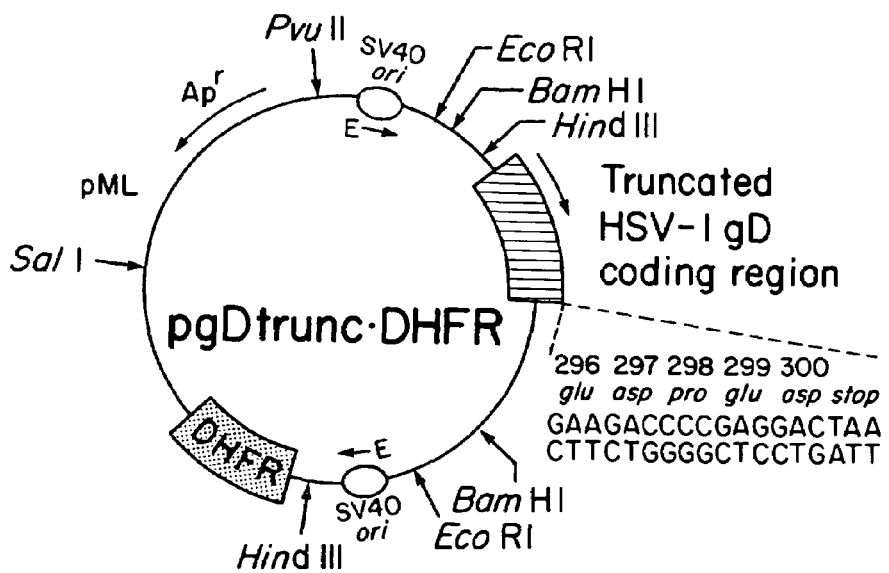
Fig. 8.

Fig.13 (Part 1)

```
         *   *** **       *** **         **   *                 ****   *
HSV-1   G-GATGGGGCCCGGGTATAAATTCCGGAAGGGGACACGGGCTACCCTCACTACCGAGGGC        60
HSV-2   GTGCCGTGTGGA-CGGGTATAAAGGCCAGGGCCAGGCGGGC--CCATCACTGTT-AGGGT
                         "TATA 1"                  -----> HSV-1 gC
                                                     mRNA 5' end

*   **     *    *   ***       *    ***   *  ****      *
HSV-1   GCTTGGGTCGGGGAGGCCGCATCGAACGC-ACACCCCATCCGGTGG---TC--CGTGTGGA       120
HSV-2   GTTAGGTTGGGGAGGTGGCACACAAAAGCGACACACACCCGTGTTGTCCGGGGGAGGC

*  ********     **          *      *  ***   *    **       **
HSV-1   GGTCGTTTTCAGTGCCCGGTC--TCGCTTTGCCGGGAACGCTAGCCGATCCCTCGCAAGG       180
HSV-2   GGTGGTTTCCGGCAACCC--TCCTCGCTCGCGCGGGCGCGCCCACCGGTCCTTCGCGGGG

***  ******   *       **                *                  *
HSV-1   GGGAGGGCG---TCGGG-CATGGCCCCCTGGGCGGGGTGGGCCTTGCCGTGTCCTGTGGGC       240
HSV-2   GCCGGGGCTCTTCTGGTCATGGCCCCTTGACGGGTGGGCCCTAACCGTGGGCCTGTGGGGC
        HSV-1 gC, HSV-2 gF initiation codons

************         *
HSV-1   CTGTTGTGGCTCGGGGCGGGGCGGGGTGGCCGGGGGGCTCGGAAACTGCCTCCACCGGCCCACG       300
HSV-2   CTGCTGTGGGTGGGTGTGGTGTCGTGGTGCTGGCCAAT-----GCCTCCCCCGGACGCACG

***      *  **                  *   *     *************
HSV-1   ATCACCGCGGGAGCGGTGACGAACGCGAGCGGAGCCCCCACATCGGGGGTCCCCGGGTCA       360
HSV-2   ATAACGGTGGGCCCGCGGGGAACGCGAGCGAGCAATGCCGCGCCCCCCTCG---------
```

Fig.13(Part 2)

```
         ****************************************************                        420
HSV-1    GCCGCCAGCCCGGAAGTCACCCCCACATCGACCCCAAACCCCAACAATGTCACACAAAAC
HSV-2    ------------------------------------------------------------

*****  ****  ***  **     *     **              *    ****  *         480
HSV-1    AAAACCACCCCACCGAGCCGGCCAGCCCCCAACAACCCCCAAGCCCACCTCCCACGCCC
HSV-2    ------GTCCCCCGGAACCGGATCCGCCCCCGAACCACACCGCCCCCCCAACCCGC

*****  *******       *******  *           ******  ******            540
HSV-1    AAAGCCCCCCACGTCCACCCCGACCCCAAACCCGACCCCAAACAACAACACCACCCCGCCAAG
HSV-2    AAGGCGACGAAAAGTAAGGCCTCCACCGCCAAACCGGCCCGCCC----CCC---AAG

*  *****  *  *     *      *       *  ***       *      **            600
HSV-1    TCGGGCCGCCCCACTAAAACCCCCGGG---CCCGTGTGGTGCGACCGCCGCGACCATTG
HSV-2    ACCGGG---CCCCCGAAGACATCCTCGGAGCCCGTGCCGATGCAACCGCCACGACCCGCTG

*                    **  *               *                          660
HSV-1    GCCCGGTACGGGCTCGCGGGGGTGCAGATCCGATGCCGGTTTCGGAATTCCACCCGCATGGAG
HSV-2    GCCCGGTACGGCTCGCGGGGGTGCAAATCCGATGCCGGTTTCCCAACTCCACCCGCACGGAG

*        *         **  ***    ***  ***           **  *              720
HSV-1    TTCGCCCTCCAGATATGGCGTTACTCCATGGGTCCGTCCCCCCAATCGCTCCGGCTCCC
HSV-2    TCCCGCCCTCCAGATCTGGCGTTATGCCACGGCCGGACGCCGAGATCGGAACGGCGCCT

** *                  **  ***                    *                  780
HSV-1    GACCTAGAGAGGAGGTCCTGACGAACATCACCGCCCACCCGGGGGACTCCTGGTGTACGAC
HSV-2    AGCTTAGAGGAGGAGGTGATGGTAAACGTGTCGGCCCCGCCGGGGGGCCAACTGGTGTATGAC
```

HSV-1
HSV-2

Fig.13(Part 3)

```
HSV-1  AGCGCCCCCAACCTGACGGACCCCCACGTGCTCTGGGCGGAGGGGCCGGCCCCGGGGCGCC  840
HSV-2  AGCGCCCCCAACGGAACGGACCCCGACGTGATCTGGGCGGAGGCGCCGCCGGCCCGGGCGCC
       **        **     ***        *        **   *  *  *     *

HSV-1  GACCCTCCGTTGTATTCTGTCACCGGGCCGCTGCCAGCCCAGCGGCTGATTATCGGCGAG  900
HSV-2  AGCCCGGGCTGTACTCGGTCGTCGGGCCGCTGGGGTCGGCAGCGGCTCATCATCGAAGAG
       *  **   *****  *** **  * *****    *    ******  ** ***   **

HSV-1  GTGACGCCCGCGACCCAGGGAATGTATTACTTGGCCTGGGCCGGATGGACAGCCCGCAC  960
HSV-2  CTGACCTTGGAGACACCCAGGGCATGTGTACTACTGGGTGTGGGGCCGGACGCCCCGCC
          *      ****        **  *   *  *        *  ***     *  *  *

HSV-1  GAGTACGGGACGTGGGGTGCGCGTCCGCATGTTCCGCCCCCCCGTCTCTGACCCTCCAGCCC  1020
HSV-2  GCGTACGGGTGGGACCTGGGGTGCGTGCGCTGTTCGCGTGTTCCGCCCTCGCTGACCATCCACCCC
        ***   **   ***    *  *    ***** *   *  *** *       **   **  **

HSV-1  CACGCGGTGATGGAGGGTCAGCGTCCGTTCAAGGCGACGTGCACGGGCCGCCTACTACCCCG  1080
HSV-2  CACGCGGTGCTGGAGGGCCAGTTCGCGTTAAGGGCCAGTTGCACGGCCGCCACCTACTACCCCG
                  *                    **  **       *   ***    **

HSV-1  CGTAACCCCGTGGAGTTTGACTGGTTCGTCTGGTTCGAGGACGACCGCCAGGTGTTTAACCCGGGGCCAG  1140
HSV-2  GGCAACCGCGCGGAGTTCGCGTTAAGGGCCAGTTGCACGGCCGCCACCTACTACCCCG
                                *      *          **   *

HSV-1  ATCGACACGCAGAGACGCACGAGCACCCGGACGGGTTCCACACAGTCTCTACCGTGACCTCC  1200
HSV-2  ATACACACGCAGAACGCAGGAGAACCCGACGACGGCTTTTCCACCGTCCACCGTGACCTCC
       **   *      *    **  *  * *  *      *    ** **     * *****

HSV-1  GAGGCTGTCGGCGGCCCAGGTCCCCGGGACCCTTCACCTGCCAGATGACGTGGCATCGC  1260
HSV-2  GCGGCCGTCGGCGGCCCAGGCCCCCCGGCCCACCTTCACCTTGCCAGCTGACGTGGCACCGC
         *** ************      **        ****    ***** *************
```

Fig.13(Part 4)

```
HSV-1  GACTCCGTGACGTTCTCGCGACGCAATGCCACCGGGCTGGCCTTGGTGCTGCCGCGGCCA    1320
HSV-2  GACTCCGTGTCGTTCTCTCGGGCGACGCAACGCCAGCAGCCACGGCCATCGGTGCTGCCGGCCA

HSV-1  ACCATCACCATGGAATTTGGGGTCCGGCATGTGGTCTGCACGGCCGGCTGCGTCCCCGAG    1380
HSV-2  ACCATTACCATGGAGTTTACGGGGTCCGGCATGTGGTCTGCACGGCCGGCTGCGTCCCCGAG

HSV-1  GGCGTGACGTTTGCCCTGGTTCCCTGGGGGACGACCCCTCACCGGGGCTAAGTCGGCCGTT    1440
HSV-2  GGGGTGACGTTTGCCTGGTTCCCTGGGGGACGACTCCTCGCCCGGGGAGAAGGTGGCCGTC

HSV-1  ACGGCCCAGGAGTCGTGCGACCACCCCCGGGCTGGCTACGGTCCGGTCCACCCTGCCCATT    1500
HSV-2  GCGTCCCAGAGACATCGTGCGGGCCACCGCCCGGCCACCGCCCGATCCGCTCCACCCTGCCGGTC

HSV-1  TCGTACGACTACAGCGAGTACATCTGCTGGTTGACCGGGATATCCGGCGGGATTCCCGTT    1560
HSV-2  TCGTACGAGCAGACCAGACCGAGTACATCTGCCGGCGGCTGCCGGCTACCCGGGGACGGAATTCCGGTC

HSV-1  CTAGAGCACCACCGGCAGTCACCAGCCCCCACCCAGGACCCCACCGAGCGGCAGGTGATC    1620
HSV-2  CTAGAGCACCACCGGCAGCAGCCAGCCCCCGCGGGGACCCCACCGAGCGGCGGCAGGTGATC

HSV-1  GAGGCGATCGAGTGGGTGGGGTGGGGATTGGAATCGGGGGTTCTCGCGGCGGGGTCCTGGTCGTA    1680
HSV-2  CGGGGCGGGTGGAGGGGCGGGGATCGGAGTGGCTGTCCTTGTCGCGGCGGTGGTTCTGGCCGGG
```

Fig.13(Part 5)

```
                *     **   **  ***  **   **  *  *    **      *
HSV-1    ACGGCAATCGTGTACGTCGTCCGCACATCACAGTCGGCGGCAGCGTCATCGGCGGTAACGC     1740
HSV-2    ACGCGGGTAGTGTACCTCACCCAGCGCCTCCTCGGTGCGCGCTATCGTCGGCTGCGGTAACTC
                                                   HSV-1 gC, HSV-2 gF
                                                    termination codons
          **  *****  *******  *******   *  *** *****  *** *   *
HSV-1    GAGACCCCCCCGTTACCTTTTAATATCTATATAGTTTGGTCCCCCTT---CTATCCCG      1800
HSV-2    CGGGGCCGGGCCCGGCCCGCCCGGT-TGTCTTCTTT-TCCACCCCCTTCCGTCCCCGTACCC

*   **  ***** *********  *  *       *   *****     *****
HSV-1    CC-------------CACCGCTGGGCGCTATAAAGCC-GCCACCCCTC                1860
HSV-2    ACCACACCCCACCCCACCCCCCCGCGTCCCCGGGGCGTTATAAGC--CGCCGCACTCGC
                                              "TATA 2"
           ***  *******     *****   **  **** **  * ****** *   *****
HSV-1    TTCCCTCAGGTC---ATCCTTGGTC-GATCCCGAACGAGACACGGCGTGGAG---CAAAA    1920
HSV-2    TTTTCCACCGGAAAATCCTCGGCCCGGCCCGATCC-GAACGGGCCACGCCGCGTGGGCTCCAAA

****   ******   ***** ****** ** ** **  ****  *  *  ******
HSV-1    CGCCTCCCCCTGAGCC-GCTTTCCTACCAACACACCGGCATGCC----T-CT--G-----    1980
HSV-2    CGCCTCCGGAAGAGAGCGCCCCCCGCCCCGAT-ATTCAAGCCCGGTGGTGCTGCTATGGCTTT
                                                  HSV-2 second open reading
                                                    frame initiation codon
          *    *     ***    *  *   ****   ***** ********** *******
HSV-1    -CGGGCATCGGAACAGCC-TACCGGCCCCTGGGCCCCGGGACACCCCCCATGCGGGCTCG    2040
HSV-2    CCGTGCTTCGGGACCCGCCTACCAGCCCCTCGCCCCGGCCTCCCCCCGGCGGCGGGGCTCG
                                                        730 bp HSV-1 mRNA
                                                         initiation codon
```

Fig.13(Part 6)

```
         *** *        *      ***       *       ***    *    *
HSV-1   GCTCCCCGCCGCGGCCTGGGTTGGCGTCGGGACCATCATCGGGGGAGTTGTGATCATTGC   2100
HSV-2   TGTTCCGGCCGTGGCCTGGATCGGCGTCGGAGCGGATCGTCGGGGCCTTTCGGCTCGTCGC
            *          *    *       ***          *       *
HSV-1   CGCGTTGGTCCTCGTGCCCTCGCGGGCCTCGTGGGAGCCACTTTCCCCACAGCGGATG    2160
HSV-2   CGCGTTGGTTCTCGTACCCCCTCGGTCCTCGTGGGGGGACTCTGCCCGTGCGACAGCGGCTG
          *  *        *         *** *         ***    *   *   *
HSV-1   GCACGAGTTCAACCTCGGGTGCATATCCTGGGATCCGACCCCCATGGAGCACGAGCAGGC   2220
HSV-2   GCAGGAATTCAACGCGGGATGCGTCGGGTGGGGACCACCCCCCGTCGAGCGAGCACGAGGC
          *        *         *        *    *       **    *   *
HSV-1   GGTCGGCGGCTGTAGGCGCCCCCGGGCGACCCTGATCCCCCGCGCGGCTGCCAAACAGCTGGC   2280
HSV-2   GGTCGGCGGCTGCAGCGCCGTCGCGCGCCACCCTTATCCCCCGTGCGCCCAAGCACCTGGC
          ** **          *        *         *                *   *
HSV-1   CGCCGTCGCGCACACGCGTCCAGTCGGCAAGATCCTCGGGCTACTGGTGGGTGAGCGGAGACGG   2340
HSV-2   CGCTCTGACACACGCGTCCAGGCGGAGAGATCGTCGGGTTACTGGTTGGTGGGTGAACGGGAGACGG
          *    *  *     *            *    **  *     *    *    *
HSV-1   CATTCGGGCCCGCCCTGCGGCTCGTCGACGGCGTTGGCGGTATTGACCAGTTTTGCGAGGA   2400
HSV-2   CATCCCGGACCTGTCTCTGAGACTCGTCGACAGCGTCAGTGGCATGGCATCGACGAGTTTTGCGAGGA
         *
HSV-1   GCCCGCCCTTCGGCATATGCTACTATCCCCGCAGTCCCGGGGGCTTTGTTCAGTTTGTAAC   2460
HSV-2   GCTC
         *
HSV-1   TTCGACCCCGCAACGCGCTGGGGCTGCCGTGA                              2491
```

Fig. 15 (Part 1)

```
              C           C      C CC CCCN         C  CC      C   CN      C CC      C CC
              *           *      * ** ****         *  **      *   * *     * **      * **
HSV-1 gC    1 MAPGRVGLAVVLWGLLWLGAGVAGGSETASTGPTITAGAVTNASEAPTS
HSV-2 gF      MALGRVGLAVGLWGLLWGLLWVGVVVVLANASPGRTITVGPRGNASNAAPS

NCNCC  N  CNCN  CCNC  ****
                                    ************ ****   *  ****  ****  ****
HSV-1 gC   50 GSPGSAASPEVTPTSTPNPNKYTPNKTPTEPASPPTTPKPTSTPKSPPT
HSV-2 gF   48 ------------------------VPRNYTAPRTTPTPPQPRKATKS

NCCNC  NNN       C      C   CCC     N  N      C
              ****   ***       *      *   ***     *  *      *
HSV-1 gC  101 STPDPKPKNYTPAKSGRPTKPPG-PVWQDRRDPLARYGSRVQIRQRFRN
HSV-2 gF   71 KASTAKPAPP---P-KTG-PPKTSSEPVRQNRHDPLARYGSRVQIRQRFPN

C  C              CCCCNCC  CC  **    CC CC      N
              *  *              ********  **        **  **      *
HSV-1 gC  150 SRMEFRLQIWRYSMGPSPPIAPAPDLEEVLTKKAPPGLLVYDSAPN
HSV-2 gF  117 SRRTESRLQIWRYATATDAEIGTAPSLEEVMKKAPPGGQLVYDSAPR

C                         C  CN      C CCC        NC
              *                         *  * *     * ***        **
HSV-1 gC  200 DPHVLWAEGAGPGADPPLYSVTGPLPTQRLIIGEVTPATQGMYYLAWGR
HSV-2 gF  167 DPHVIWAEGAGPGASPRLYSVVGPLGRQRLIIEELTLETQGMYYWVWGR
```

Fig. 15 (Part 2)

```
               C  N NC              C         CC    C             C     N NC
               *  * **              *         **    *             *     * **
HSV-1 gC  250  MDSPHEYGTWVRVRMFRPPSLTLQPHAVMEGQPFKAT[C]TAAAYYPRNPVE
HSV-2 gF  217  TDRPSAYGTWVRVRVFRPPSLTIHPHAVLEGQPFKAT[C]TAATYYPGNRAE

N     N  NC     N          CC     C      C           C
               *     *  **     *          **     *      *           *
HSV-1 gC  300  FDWFEDDRQVFNPGQIDTQTHEHPDGFTTVSTVTSEAVGGQVPPRTFT[C]
HSV-2 gF  267  FVWFEDGRRVFDPAQIHTQTQENPDGFSTVSTVTSAAVGGQPPRTFT[C]

C                    C   C   CCN   C          C      C
               *                    *   *   ***   *          *      *
HSV-1 gC  350  MTWHRDSVTFSRR[NAT]GLALVLPRPTITMEFGVRHVV[C]TAG[C]VPEGVTFA
HSV-2 gF  317  LTWHRDSVSFSRR[NAS]GTASVLPRPTITMEFTGDHAV[C]TAG[C]VPEGVTFA

C      CCC  C        NC  C      C CCC     N C
                    *      ***  *        **  *      * ***     * *
HSV-1 gC  400  WFLGDDPSPAAKSAVTAQES[C]HPGLATVRSTLPISYDYSEYI[C]WLTGYP
HSV-2 gF  367  WFLGDDSSPAEKVAVASQTS[C]GRPGTATIRSTLPVSYEQTEYI[C]RLAGYP

N  C CC   CC  CCC   C      C C
                                      *  * **   **  ***   *      * *
HSV-1 gC  450  AGIPVLEHHGSHQPPPRDPTERQVIEAIEWVGIGIGVLAAGVLVVTAIVY
HSV-2 gF  417  DGIPVLEHHGSHQPPPRDPTERQVIRAVEGAGIGVAVLVAVVLAGTAVVY

CCCC NN  N  NN
               **** **  *  **
HSV-1 gC  500  VVRTSQSRQRHRR
HSV-2 gF  467  LTHASSVRYRRLR
```

Fig.15 (Part 3)

```
                                   C *   C  C   C *  C C   CC CCCCC
                                   * *********  *    *  *  ** *****
HSV-2 730bp ORF    1   MAFRASGPAYQPLAPRPPPARARVPAVAWIGVGAIVGAFALVAALVLVP
HSV-1 730bp ORF    1   ---------------------MRARLPAAAWVGVGTIIGGVVIIAALVLVP

C C  C      C         C   C  CC      C
                       * *  *      *         *   *  **      *
HSV-2 730bp ORF   50   PRSSWGLCPCDSGWQEFNAGCVAWDPTPVEHEQAVGGCSAPATLIPRAAA
HSV-1 730bp ORF   31   SRASWALSPCDSGWHEFNLGCISWDPTPMEHEQAVGGCSAPATLIPRAAA

C  CC     C          N      CN     C C   N    C
                          *  **     *          *      **     * *   *    *
HSV-2 730bp ORF  100   KHLAALTRVQAERSSGYWWVNGDGIRTCLRLVDSVSGIDGFCEEL
HSV-1 730bp ORF   81   KQLAAVARVQSARSSGYWWVSGDGIRARLRLVDGVGGIDQFCEEPALRIC

HSV-1 730bp ORF  131   YYPRSPGGFVQFVTSTRNALGLP
```

IMMUNOGENIC COMPOSITION BASED ON A TRUNCATED DERIVATIVE OF A MEMBRANE BOUND PROTEIN AND PROCESS FOR MAKING IT

This application is a continuing application (35 USC 120) of application Ser. No. 08/357,084 filed 15 Dec. 1994, now U.S. Pat. No. 5,851,533, which is a continuing application of Ser. No. 08/171,858 filed 21 Dec. 1993, now abandoned, which is a continuing application of Ser. No. 07/814,243 filed 23 Dec. 1991, now abandoned, which is a continuing application of Ser. No. 07/695,585 filed 3 May 1991, now abandoned, which is a continuing application of Ser. No. 06/878,087 filed 24 Jun. 1986, now abandoned, which is a continuing application of Ser. No. 06/588,170 filed 9 Mar. 1984, now abandoned, which is a continuing application of Ser. No. 06/547,551 filed 31 Oct. 1983, now abandoned, which is a continuing application of Ser. No. 06/527,917, now abandoned, filed 30 Aug. 1983.

This invention relates to membrane bound proteins and derivatives thereof, and to vaccines obtained from them.

BACKGROUND

Analysis of the immune response to a variety of infectious agents has been limited by the fact that it has often proved difficult to culture pathogens in quantities sufficient to permit the isolation of important cell surface antigens. The advent of molecular cloning has overcome some of these limitations by providing a means whereby gene products from pathogenic agents can be expressed in virtually unlimited quantities in a non-pathogenic form. Surface antigens from such viruses as influenza (1), foot and mouth disease (2), hepatitis (3), vesicular stomatitis virus (4), rabies (5), and herpes simplex viruses (6) have now been expressed in E. coli and S. cerevisiae, and, in the future, promise to provide improved subunit vaccines. It is clear, however, that the expression of surface antigens in lower organisms is not entirely satisfactory in that potentially significant antigenic determinants may be lost by virtue of incomplete processing (e.g., proteolysis, glycosylation) or by denaturation during the purification of the cloned gene product.

This is particularly true in the case of membrane proteins, which, because of hydrophobic transmembrane domains, tend to aggregate and become insoluble when expressed in E. coli. Cloned genes coding for membrane proteins can be expressed in mammalian cells where the host cell provides the factors necessary for proper processing, polypeptide folding, and incorporation into the cell membrane (7,8). While these studies show that membrane proteins can be expressed on the surface of a recombinant host cell, and, for example (8), that a truncated membrane protein lacking the hydrophobic carboxy-terminal domain can be slowly secreted from the host cell rather than be bound to it, it is not clear that either the membrane-bound protein thus expressed or the truncated protein thus secreted will be able to act, in fact, to raise antibodies effective against the pathogen from which the protein is derived.

Herpes Simplex Virus (HSV) is a large DNA virus which occurs in two related, but distinguishable, forms in human infections. At least four of the large number of virus-encoded proteins have been found to be glycosylated and present on the surface of both the virion and the infected cells (9). These glycoproteins, termed gA/B, gC, gD, and gE, are found in both HSV type 1 (HSV1) and HSV type 2 (HSV2), while in the case of HSV 2, an additional glycoprotein (gF) has been reported to be found (10). Although their functions remain somewhat of a mystery, these glycoproteins are undoubtedly involved in virus attachment to cells, cell fusion, and a variety of host immunological responses to virus infection (11). Although HSV 1 and HSV 2 show only ~50 percent DNA sequence homology (12), the glycoproteins appear to be, for the most part, type-common. Thus, gA/B, gD, and gE show a large number of type-common antigenic determinants (13-16), while gC, which was previously thought to be completely type-specific (17, 18), has also been found to possess some type-common determinants. Type-specific antigenic determinants can, however, be demonstrated using monoclonal antibodies for some of the glycoproteins (10,19), showing that some amino acid charges have occurred since HSV1 and HSV2 diverged.

One of the most important glycoproteins with respect to virus neutralization is gD (11). Considerable evidence has been adduced strongly suggesting that the respective gD proteins of HSV-1 and HSV-2 are related. For example, recombination mapping has localized the respective genes to colinear regions in both virus genomes. Amino acid analysis showed gross homology between the two proteins. The gD proteins induce neutralizing antibodies to both type 1 and type-2 viruses in a type-common manner (19-21). In addition, most monoclonal antibodies generated to these glycoproteins are type common, also suggesting a high degree of structural relatedness between the two types of glycoproteins (20). Some monoclonal antibodies, however, were found to react type-specifically, suggesting significant differences between the proteins (19). Peptide maps of the proteins also unambiguously revealed such differences (22a). These results although suggesting that these polypeptides are related, are insufficient to indicate exactly how close the relationship is.

In order to examine the nature of the type-commonality of HSV-1 and HSV-2 gD proteins, the DNA sequences of the gD genes from HSV1 and HSV2 were determined. The derived amino acid sequences showed similarity. The resultant derived protein sequences were also analyzed for structural differences by using a program designed to determine hydrophobic and hydrophilic regions of the protein. This analysis demonstrated a high degree of conservation on a gross structural level. Although several amino substitutions were found between the two glycoproteins, the vast majority of these substitutions were conservative, suggesting an important structural requirement of this glycoprotein to the virus.

In contrast to HSV-1, HSV-2 appears to encode yet another glycoprotein, termed gF (22b,10,22c,22d). Although the HSV-2 gF had an electrophoretic mobility which was much faster than HSV-1 gC, mapping studies with recombinant viruses revealed that this protein was encoded by a region of the HSV-2 genome which was approximately colinear with the gene for HSV-1 gC (22c, 22d). In addition, it has been recently demonstrated that a monoclonal antibody against HSV-2 gF will cross-react weakly with HSV-1 gC (22f) and that a polyclonal antiserum made against HSV-1 virion envelope proteins precipitated gF (22d), suggesting a possible structural homology between the two glycoproteins. Thus, it appeared that a possible homologue to HSV-1 gC was the HSV-2 gF protein. This relationship was investigated in accordance with the present invention.

To examine the relatedness between HSV-1 and HSV-2, it has been determined herein that a DNA sequence of a 2.29 kb region of the HSV-2 genome is colinear with the HSV-1 gC gene. Translation of a large open reading frame in this region demonstrates that a protein which has significant homology to HSV-1 gC is encoded in this region. It is suggested that this region encodes the HSV-2 gF gene and that the gF protein is the HSV-2 homologue of HSV-1 glycoprotein C.

SUMMARY OF THE INVENTION

One specific embodiment of the invention relates to a vaccine based on the gD protein. In the light of this information about the structure of the gD protein, as described more fully herein, it was decided to express the gD protein DNA in mammalian cells to see whether such was possible, and if possible, whether the expressed protein would bind to the host cell membrane, and whether a truncated form of protein lacking the membrane-binding domain would be secreted from the host cell, and in either of the latter cases whether the expression product proteins could raise antibodies effective against HSV-1 and/or HSV-2. As the results herein demonstrate, these objects have been achieved. In particular, the invention provides using these proteins obtained by recombinant DNA processes as components in a vaccine effective against HSV-1 and HSV-2 viruses. Thus provided are protective vaccines against occurrence of herpes infection and of reduction in frequency and severity of herpes infection recurrence in individuals already infected.

Another specific embodiment relates to another class of glycoproteins obtained by recombinant DNA processes useful as components in a vaccine against HSV-1 and/or HSV-2 viruses. Specifically, such glycoprotein class includes HSV-1 gC (effective against HSV-1), HSV-2 gF (more properly referred to as an HSV-2 gC), effective against HSV-2, or combinations of the two proteins, effective against both viruses. Other such glycoproteins include gA, gB, and gE. It is believed that a vaccine based upon the combined gC and gD glycoproteins would be significantly more effective as a vaccine than either glycoprotein alone.

To further summarize, the present invention involves a vaccine comprising a polypeptide with antigenic determinants capable of specifically raising complementary antibody against HSV-1 and HSV-2 viruses. In one embodiment, the polypeptide is functionally associated with the surface membrane of a recombinant host cell capable of its production. In a typical instance, such functional association comprises a binding of the polypeptide with the surface membrane so that the polypeptide projects through the membrane. The recombinant cell line is derived from a stable, continuous line.

In another embodiment, the vaccine comprises a polypeptide with the same antigenic determinants, but which is not functionally associated with the surface membrane. As set out in more detail below, one such polypeptide is a truncated, membrane-free derivative of a membrane-bound polypeptide. The derivative is formed by omission of a membrane-binding domain from the polypeptide, allowing it to be secreted from the recombinant host cell system in which it has been produced.

In another embodiment, the polypeptide is formed first in functional association with a surface membrane and thereafter the polypeptide is dissolved, preferably in a non-ionic surfactant, to free the polypeptide of the membrane.

As used herein, the term "recombinant" refers to cells which have been transfected with vectors constructed using recombinant DNA technology and thus transformed with the capability of producing the polypeptide hereof. "Functional association" is meant being bound to the membrane, typically by projecting to both sides of the membrane, in such manner as to expose antigenic determinants folded in a native conformation recognizable by antibody elicited against the native pathogen. "Membrane-bound" in reference to polypeptides hereof refers to a class of polypeptides ordinarily produced in eukaryotic cells and characterized by having a signal sequence which is believed to assist its secretion through various cell membranes as well as a membrane-binding domain (usually hydrophobic in nature and occurring at the C-terminal end) which is thought to preclude its complete secretion through the cell membrane. As such, it remains functionally associated or bound to the membrane. This invention is particularly directed to the exploitation of those membrane-bound polypeptides associated with pathogenic organisms, e.g., herpes virus. The polypeptides of the invention are capable of raising neutralizing antibodies against in vivo challenge by a pathogen.

As used herein, the terms "HSV-2 gF", "HSV-2 gC" and "gC-2" are used interchangeably to refer to a glycoprotein portion of HSV-2 which is highly homologous with HSV-1 gC and which is capable of raising sufficient antibodies to be useful as a vaccine.

Once the antigenic determinants of the polypeptides of the present invention are provided by functional association with the surface membrane, thereafter, the membrane may be removed from the polypeptides without destroying the antigenic characteristics. Thus, for example, the membrane-bound polypeptide may be removed from the membrane by solubilization with a suitable solution, preferably one containing a non-ionic surfactant, to remove the polypeptide from the membrane. An advantage of doing this is to isolate the polypeptide from extraneous cellular material, raising potential potency in its use in a vaccine. A technique for removing the membrane from the polypeptide is described below.

In another embodiment, membrane-free preparations may be obtained by creation of a secretion system. As described in more detail below, such secreted polypeptide possesses at least some of the antigenic sites necessary for antibody stimulation.

In the accompanying drawings:

FIGS. 1A and 1B show the DNA and deduced amino acid sequences of the HSV-1 and HSV-2 gD genes and surrounding flanking regions;

FIGS. 4A and 4B show the result of labelling of gD12 cells with human antibodies against HSV, (A) being a visualization with phase contrast optics, (B) a fluorescence image of the same cells;

FIG. 8 is a diagram of the expression plasmid pgDtrunc-dhfr for a secreted form of HSV-1 gD protein.

Figure 11:
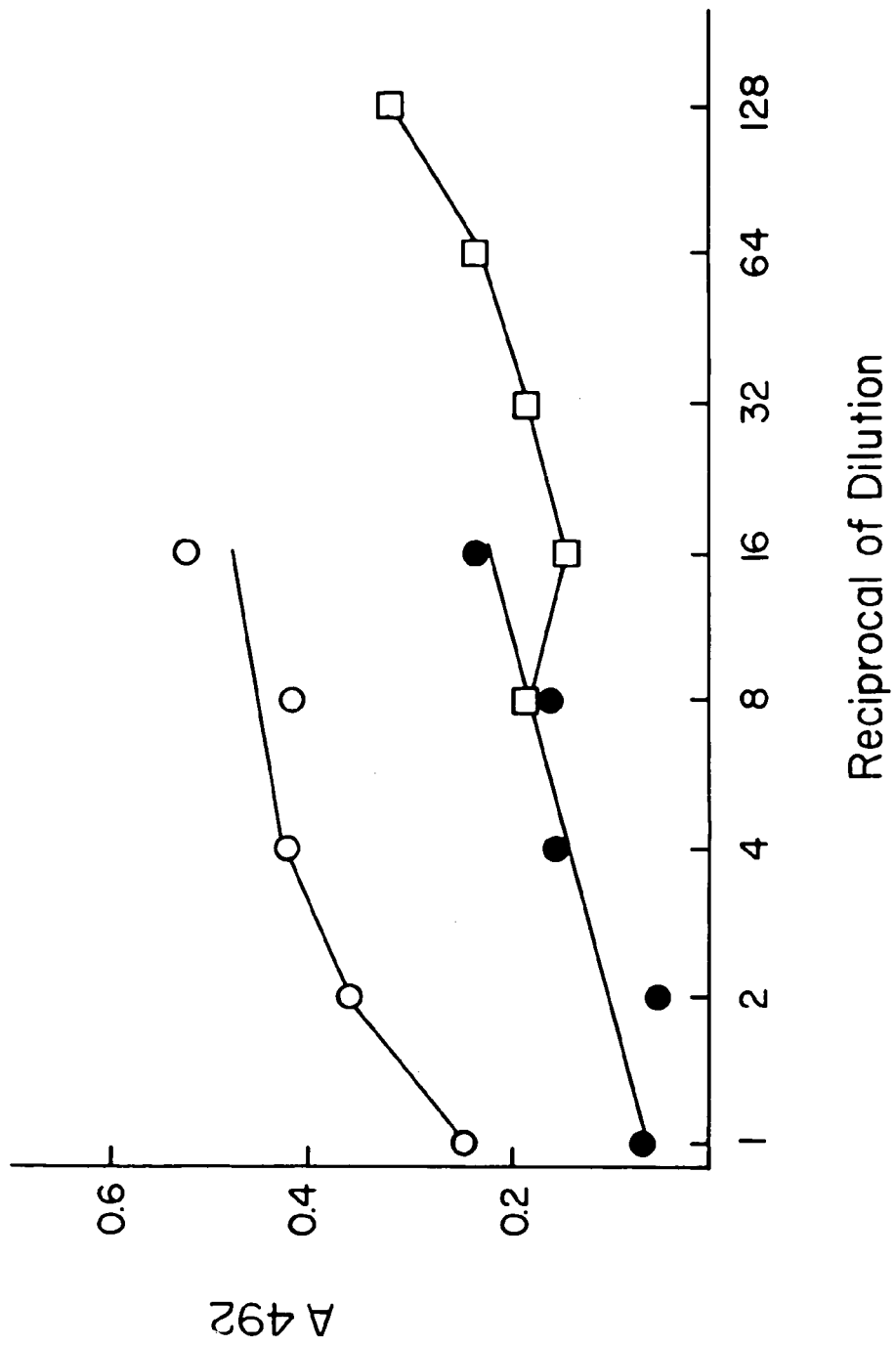

FIG. 11 demonstrates the degree of amplification achieved with the Mtx amplified gD10.2 cell line.

Figure 12:
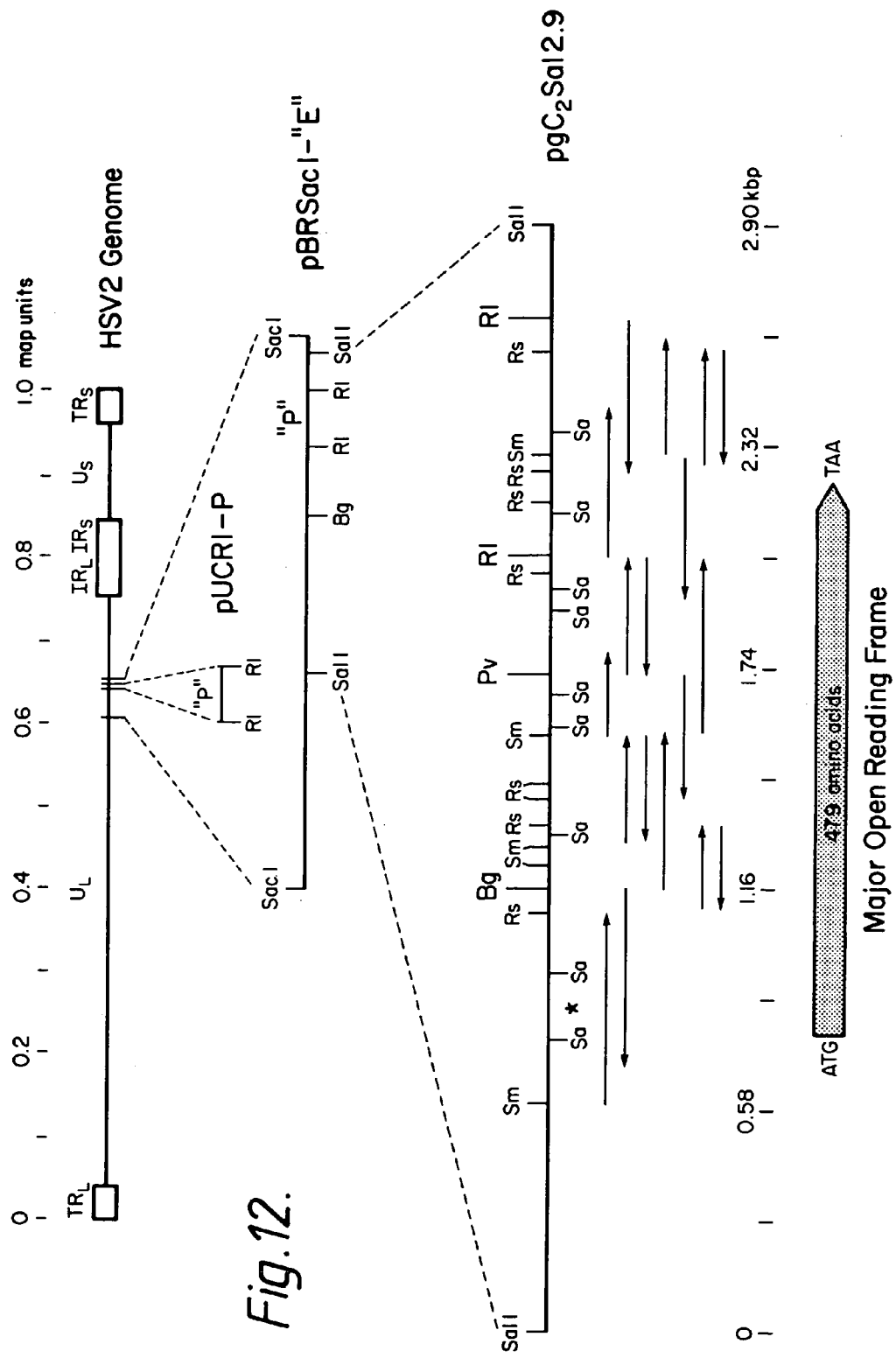

FIG. 12 shows the fragments of pgC₂Sal2.9 which were subjected to DNA sequence analysis.

FIG. 13 shows the DNA sequence derived from pgC₂SAl2.9 compared with the DNA sequence of the HSV-1 gC region.

Figure 14:
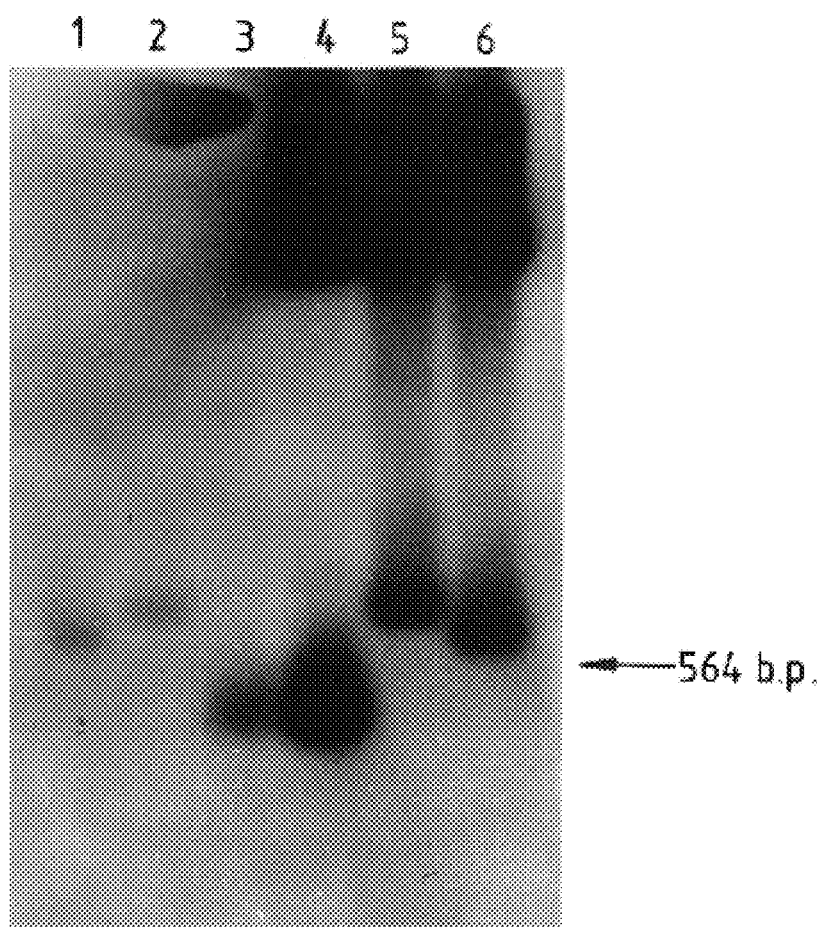

FIG. 14 illustrates southern blot analysis of HSV-2 genomic DNA and pgC₂Sal2.9 DNA.

FIGS. 15A and 15B illustrate translation of the HSV-2 large open reading frame and comparison with the HSV-1 gC amino acid sequence.

Figure 16:
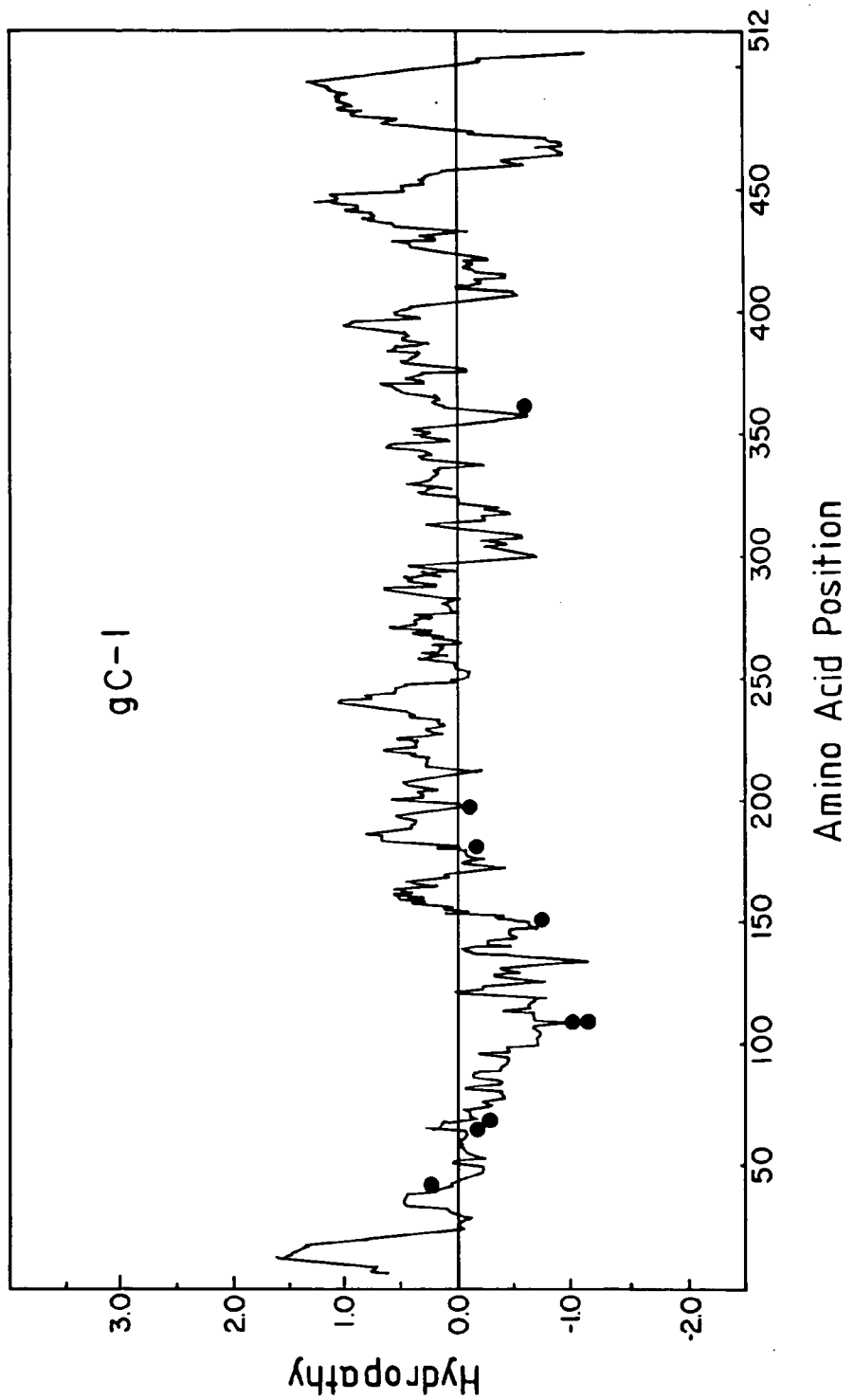
Figure 16:
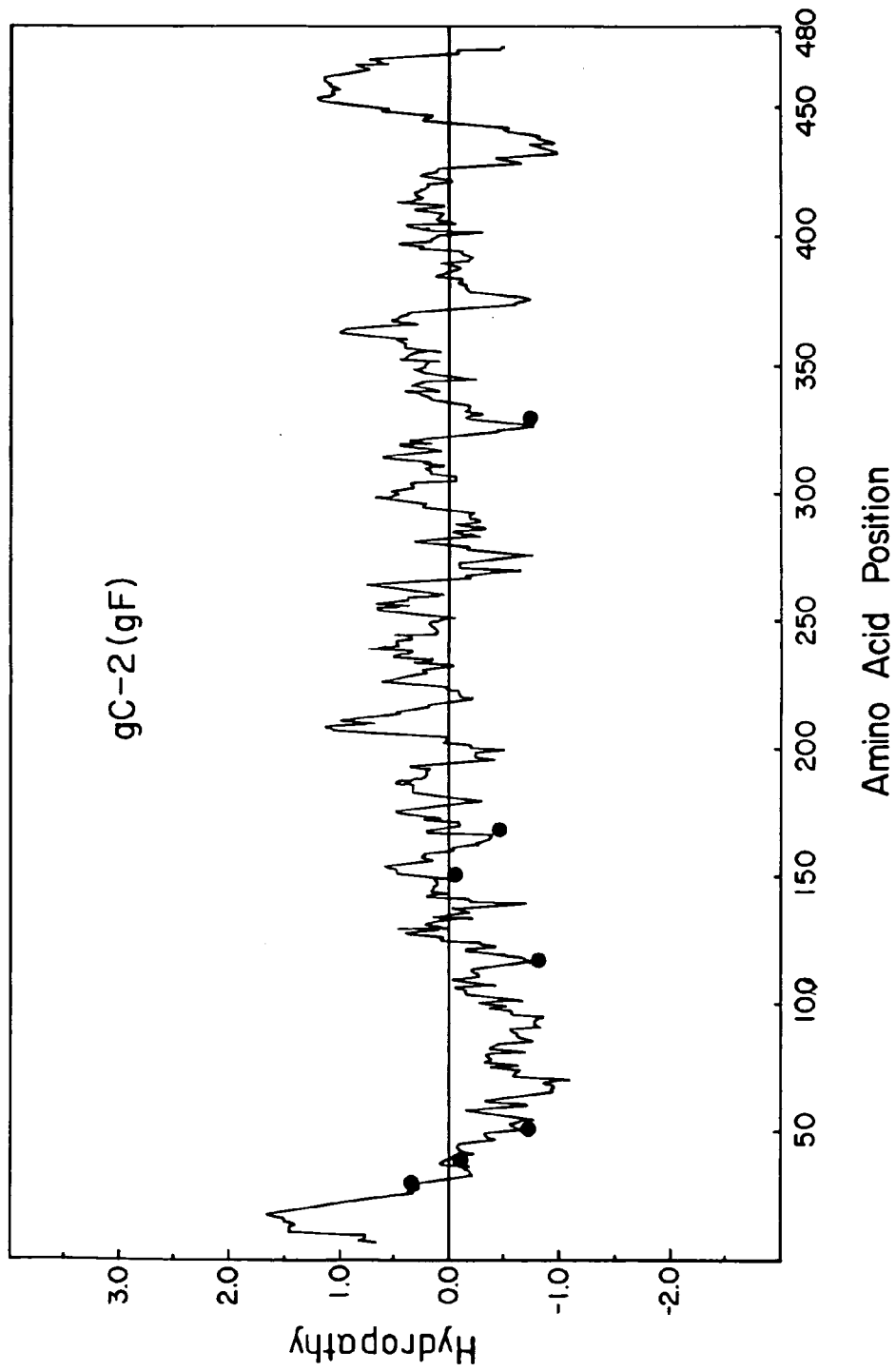

FIG. 16 illustrates hydropathy analysis of the HSV-1 gC protein and the HSV-2 major open reading frame protein.

DETAILED DESCRIPTION (EXAMPLES)

Example 1

Example 1 Relates to gD Protein

Virus Growth and Viral DNA Isolation

HSV1 (strain Hzt) and HSV2 (strain G) were grown on Hep 2 cells at 37° C. and at 33° C., respectively. The viral DNA was isolated from infected cell cultures by proteinase K digestion and CsCl banding (23).

Cloning of the gD Genes of HSV1 and HSV2

Previous mapping and cloning studies had localized the HSV1 gD gene to a ~6.6 kb Bam HI fragment (6,24). HSV1 DNA was cleaved with Bam HI, and the 6-7 kb region was isolated by agarose gel electrophoresis. This fragment was ligated into Bam HI-digested pBR322, and the resultant mixture was used to transform *E. coli* strain 294 (ATCC No. 31446). The ampicillin resistant, tetracycline sensitive plasmids were screened for the proper HSV1 fragment by restriction enzyme digestion. The correct gD containing Sst 1 fragment was subcloned into Sst 1-digested plasmid pFM3 (European Patent Application Publication No. 0068693; 5 Jan. 1983).

Although the gD gene from HSV2 was previously mapped by recombination with HSV1, the exact location of this gene was unknown. Therefore, an ~10 kb Hind III fragment from the small unique region of the HSV2 genome (4) was ligated into the Hind III site of the bacteriophage lambda cloning vector 590 (25). In vitro packaged phage were plated at low density and screened by the Benton-Davis procedure with a ³²P-labeled subclone of the gD gene from HSV1 (26). Positively hybridizing plaques were grown, the DNA isolated, and the gD gene localized by Southern blotting and hybridization with the ³²P-labeled HSV1 gD gene (27). The positively hybridizing, HSV2 gD containing fragments were subcloned into the plasmid pUC9 (28).

DNA Sequence Determination and Computer Analysis

Various fragments from the HSV1 and HSV2 gD genes were subcloned into the ml3 phage vector mp9 (29), and were sequenced by the dideoxynucleotide method of Sanger (30).

The nucleotide sequences were analyzed using the HOM program (31). The hydropathy of the deduced protein sequence was analyzed using a width of 12 and a jump of 1 (31a).

Cloning of the gD Regions from HSV1 and HSV2

Other studies had localized the HSV1 gD gene to the 6.6 kb BamHI J fragment according to the nomenclature of Roizman (6,12,24). Isolation and sequencing of part of this fragment showed that this fragment contained the HSV1 gD gene. Since one might expect that the DNA sequences of the HSV1 gD gene would be relatively homologous to the HSV2 gD gene, this fragment was used as a probe for the isolation of the gD gene from the HSV2 genome.

Since most of the genes from the HSV1 and HSV2 genomes appear to map colinearly (35), the region from the small unique region of the HSV2 genome which corresponded to the HSV1 gD region (the Hind III L fragment (12)), was cloned into a lambda phage vector. Screening of the resultant plaques with a ³²P-labeled HSV1 gD gene subclone revealed positively hybridizing plaques, suggesting that there was indeed nucleic acid sequence homology between the two virus genomes in this region. Isolation of the phage DNA and subsequent Southern blot analysis revealed the region of this fragment which corresponded to the gD gene. This region was subcloned for DNA sequence analysis.

The Coding Regions

Figure 1A:
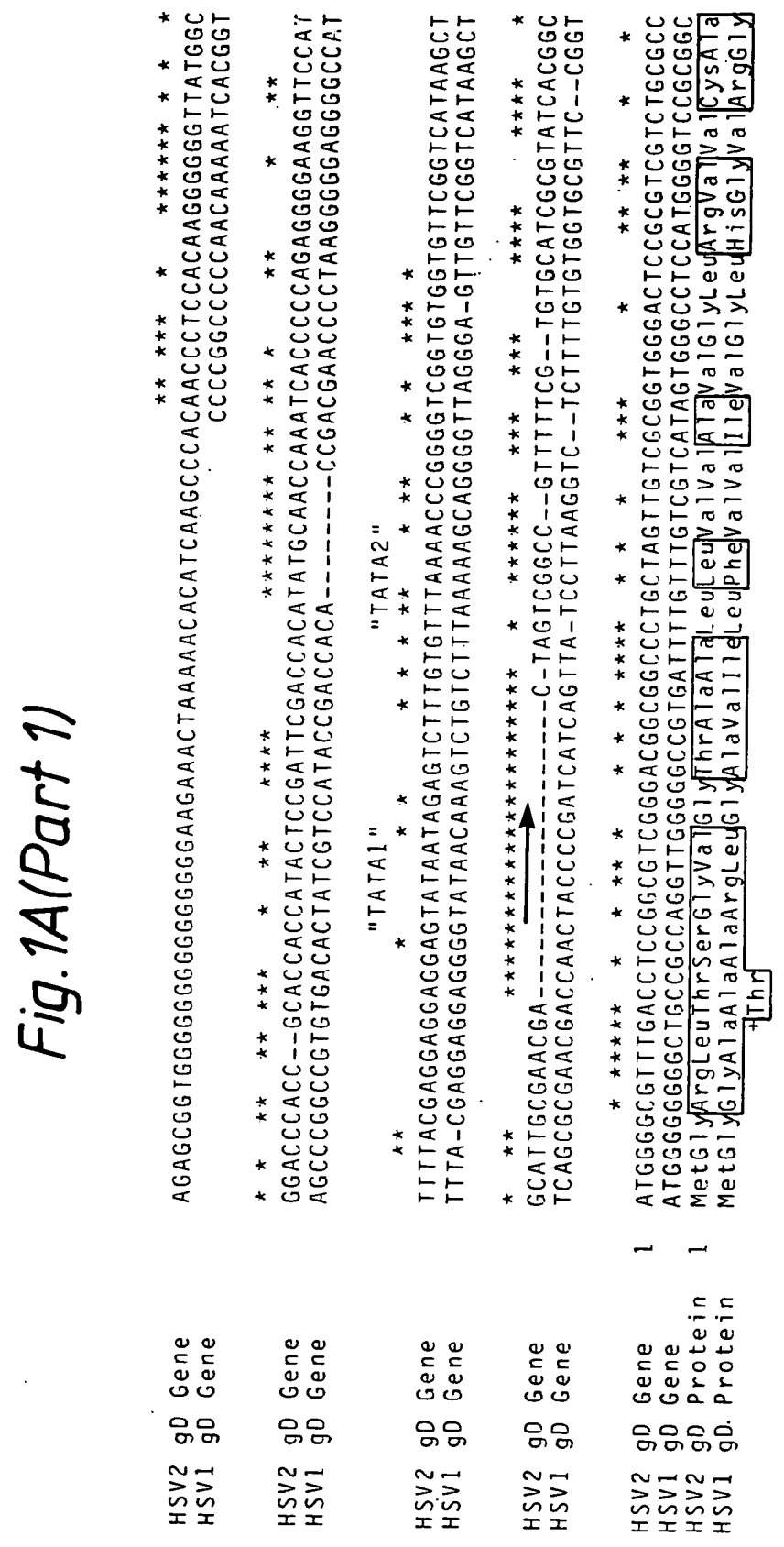

FIG. 1 illustrates the two gD DNA sequences compared with the HOM program (31). Nucleotide number 1 is chosen as the A of the ATG initiator methionine. Gaps have been introduced by the HOM computer program to maximize the sequence homologies (31). Nucleotide differences are shown by the symbol (*), while amino acid differences are shown boxed. Amino acid differences between the HSV1 gD sequence reported here, determined for the Hzt strain of HSV1, and that reported by Watson et al. (6) for the Patton strain, are depicted by the symbol (+). The start of HSV1 gD gene transcription, shown by an arrow, is from Watson et al. (32). Possible N-linked glycosylation sites are shown shaded. Two possible "TATA" sequences are shown 5 to the start of gD transcription, while a third possible "TATA" sequence is shown 5' to a second open reading frame at the 3' end of the HSV2 sequence. Two regions of non-coding sequence homology should be noted 5' to the gD genes and 5' to the second open reading frame from the HSV2 sequence.

The Hydropathy of gD Proteins

Figure 2:
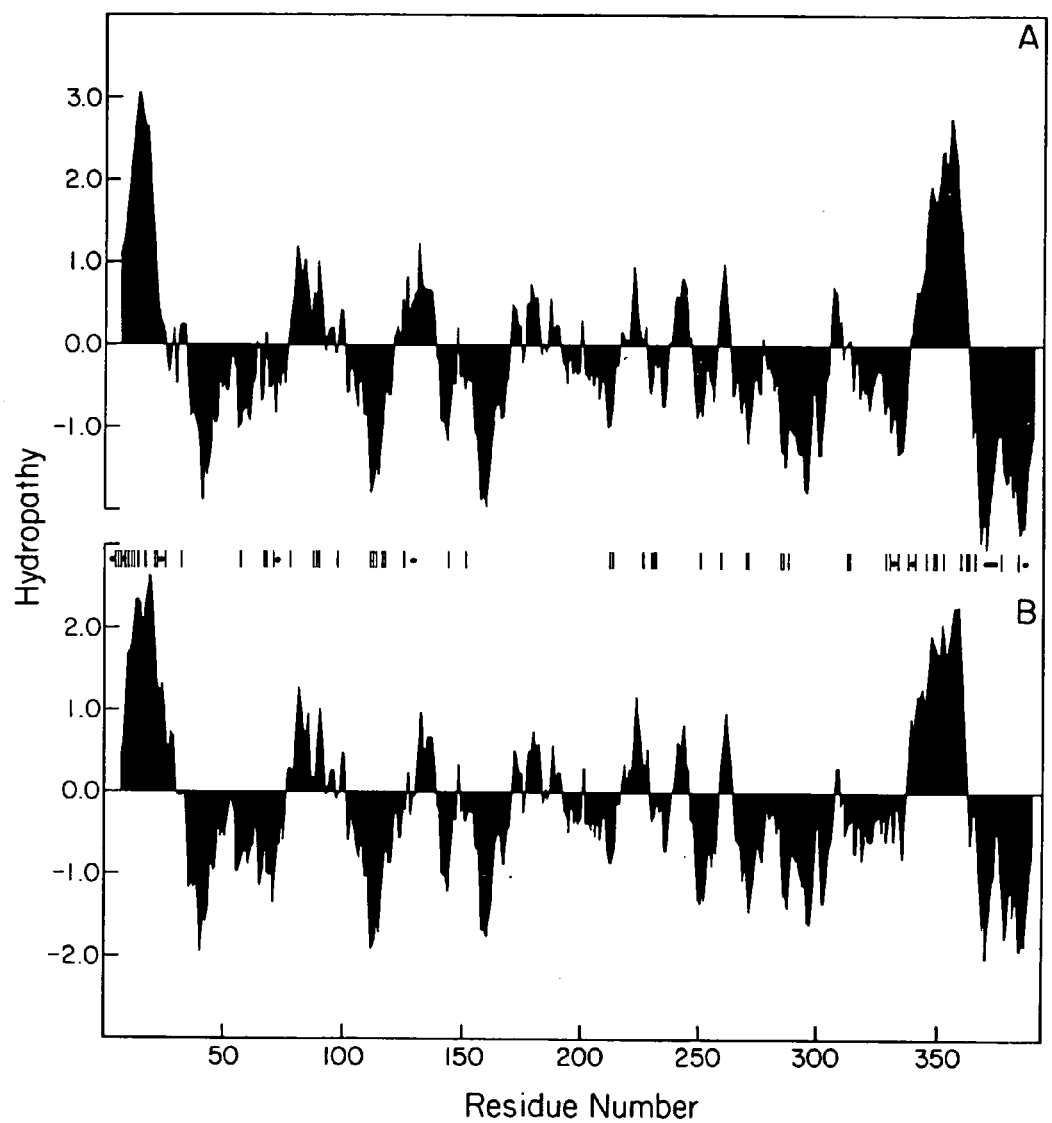
FIGS. 2A and 2B show a hydropathy analysis of the gD proteins from HSV-1 and HSV-2 proteins.

The hydropathy of each glycoprotein was analyzed using the program developed by Hopp et al. (31a). As shown in FIG. 2, a hydrophobic transmembrane domain exists at the 3'-end of the gene. Twelve amino acid long stretches were analyzed, and the average hydropathy was calculated. Residue differences between the two glycoproteins are shown, with conservative changes marked (*) and non-conservative changes marked (+). A) HSV1 gD protein hydropathy, B) HSV2 gD protein hydropathy.

The DNA sequence analysis demonstrates that the HSV1 and HSV2 gD proteins are 80 percent homologous. The majority of the differences found between these two proteins were in the amino and carboxy terminal regions. The amino-terminal region of these proteins contains a highly hydrophobic region which contains an arginine residue near the amino-terminal methionine. This hydrophobic domain is the signal sequence which is characteristic of secreted and membrane-bound proteins and which presumably functions to direct at least a portion of the protein into the lumen of the endoplasmic reticulum (33). A comparison of the first twenty amino-terminal amino acids showed that there were a total of 12 differences between the type 1 and type 2 genes. Virtually all of the differences, however, are conservative since they encode other hydrophobic amino acids. The exceptions are the gly-arg replacement at residue 3 and the arg-gly replacement at residue 7. Although these replacements are not conservative, they do not change the net structure of the signal domain. Both genes maintain a positively charged residue within the first 10 amino acids.

The hydropathy plot in FIG. 2 revealed a hydrophilic carboxy-terminal domain preceded by a hydrophobic region. This structure is characteristic of membrane-bound glycoproteins and has been previously found in other viral surface antigens (5,34). Its function is to anchor the protein in the cellular and viral membranes and, as such, performs an important role for virus infection. Twelve amino acid changes in this region of the gD proteins from residues 333 to 362 were found, most of which are conservative. This suggests that the only criterion for the amino acids in this region is that they be predominantly apolar in order to span the lipid bilayer. In addition, the region after the membrane domain (residues 363-375), which probably serves to anchor the protein in the membrane (33), shows 5 changes in its first 13 residues followed by a long homologous stretch. This result suggests that the initial 10-15 residues in the carboxy-terminal hydrophilic domain may only serve an anchoring function and therefore only need to be charged, while the subsequent 23 residues may serve some other function important to the gD protein specifically.

Although many other amino acid changes are found throughout these two proteins, the vast majority of the changes are conservative. This fact is underlined by the structure revealed by the hydropathy program shown in FIG. 2. As can be seen in this comparison, the two glycoproteins show very similar plots. The amino acid changes which are not conservative do not appear to change the hydropathy of the protein.

Expression of the HSV-1 gD

Figure 3:
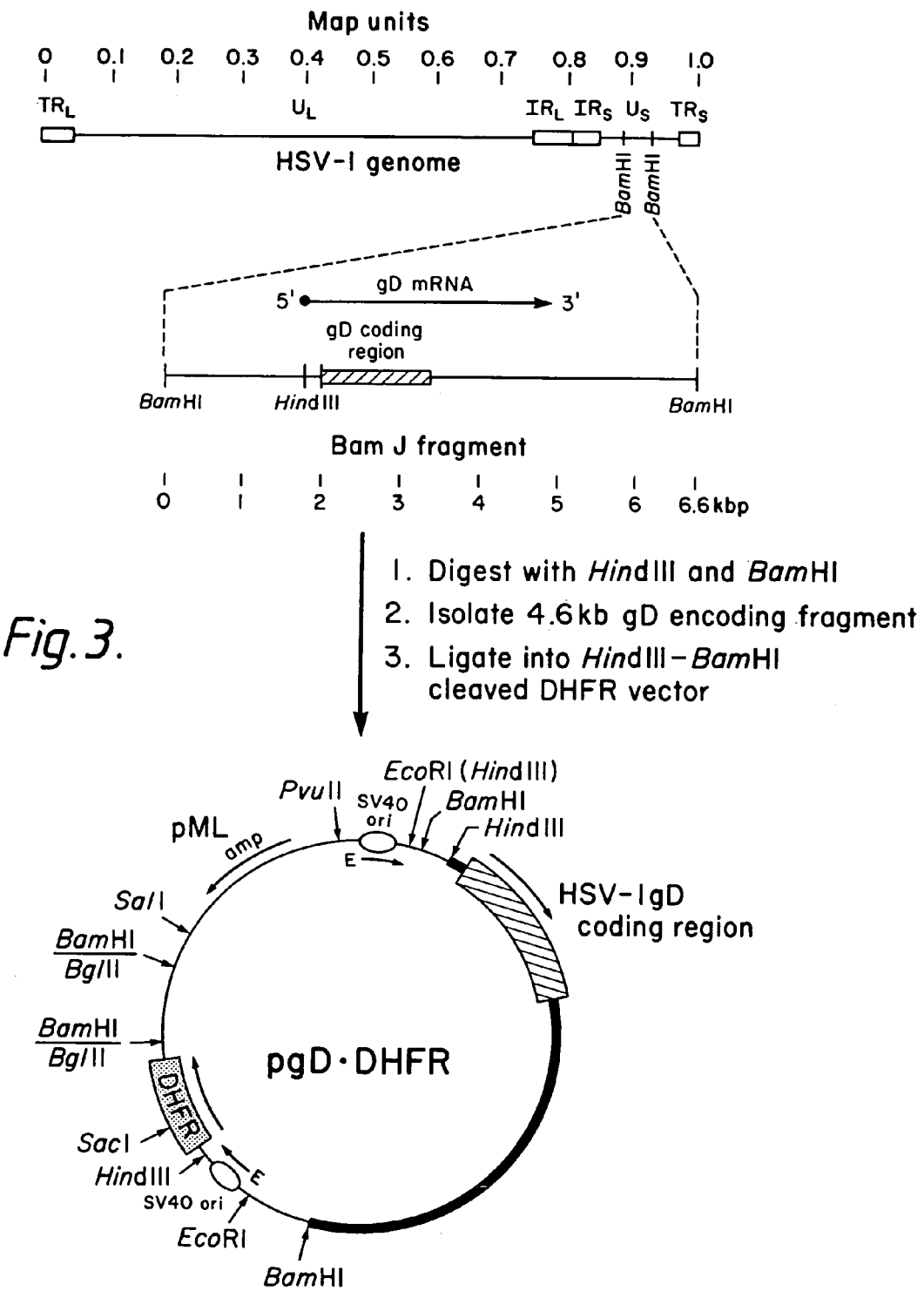
FIG. 3 is a diagram of the plasmid pgD-dhfr, constructed for the expression of a membrane-bound form of HSV-1 glycoprotein D.

In order to establish a permanent membrane-bound gD producing cell line, the gD containing fragment was ligated (FIG. 3) into a mammalian expression vector (36) containing the selectable marker, dihydrofolate reductase (dhfr). FIG. 3 shows a diagram of the plasmid, pgD-dhfr, constructed for the expression of HSV-1 glycoprotein D. The expression plasmid consisted of the origin of replication and the β-lactamase gene (amp$^r$) derived from the *E. coli* plasmid pBR322 (37), a cDNA insert encoding mouse dhfr (36,38) under control of the SV-40 early promoter and a 4.6 kb HindIII to BamHI fragment containing the gD gene also under control of the SV-40 early promoter. The HindIII end of this fragment lies 74 bp to the 5' side of the initiator methionine codon and includes the mRNA cap site. The HindIII site lies 250 bp to the 3' side of the Goldberg-Hogness box of the SV-40 promoter. The coding region of the gD-containing fragment is 1179 bp long and adjoins a large (1.9 kb) 3' region which contains at least part of the glycoprotein E gene (24,32), a translational stop codon, and a polyadenylation site.

The plasmid pgD.dhfr was constructed as follows: The 4.6 kilobase Hind III-Bam HI fragment containing the entire gD coding sequence was isolated from the Bam HI fragment cloned from the HSV 1 genome (see above). The 2.8 kilobase Hind III-Sal 1 fragment containing an SV40 origin-early promoter and the pBR322 ampicillin resistance gene and origin of DNA replication were isolated from the plasmid pEHBal 14. The 2.1 kilobase Sal 1-Bam HI fragment containing a murine dihydrofolate reductase cDNA clone under the control of a second SV40 origin-early promoter was isolated from the plasmid pE348HBV E400D22 (36). These three fragments were ligated together in a triple ligation using T4 DNA ligase, and the resultant mixture was used to transform *E. coli* strain 294. The resultant colonies were grown and the plasmid DNA screened by digestion with Sac 2. The correct DNA construction pgd.dhfr (FIG. 3) was used for further transfection studies.

The plasmid was introduced into Chinese Hamster Ovary cells (CHO) deficient in the production of dhfr (39) using a calcium phosphate precipitation method (40). Colonies capable of growth in media lacking hypoxanthine, glycine, and thymidine were obtained and nine dhfr$^+$ clones were analyzed. Of these, gD could be detected in five colonies using anti-HSV-1 antibodies in radioimmunoprecipitation and indirect immunofluorescence assays. One of the five lines (gD12) was designated for further study. In order to characterize the cloned gD gene product, gD12 cells were metabolically labeled with $^{35}$S-methionine or $^3$H-glucosamine and analyzed by radioimmunoprecipitation. The procedure used was as follows: Cells were grown in Ham's F12 medium (GIBCO) supplemented with 7 percent commercially dialyzed fetal bovine serum (GIBCO), penicillin (100 u/ml), and streptomycin (100 u/ml). When the cultures were approximately 80 percent confluent, the medium was removed, the cells were washed twice with phosphate buffered saline (PBS), and labeling medium (Dulbecco's modified Eagle's medium containing either one-tenth the normal concentration of methionine or glucose) was added to a final concentration of 0.064 ml/cm$^2$. Either $^{35}$S-methionine (SJ.204, Amersham Int.) (50-75 μCi/ml) or $^3$H-glucosamine (100 μCi/ml) was added and the cells were grown for an additional 18-20 hr. After labeling, the medium was harvested and the cells were washed twice in PBS, and removed from the culture dish by treatment with PBS containing 0.02 percent EDTA. The cells were then solubilized in lysis buffer consisting of: PBS, 3 percent NP-40, 0.1 percent bovine serum albumin, 5×10$^{-5}$ M phenylmethylsulfonyl fluoride, and 0.017 TIU/ml of apoprotinin and the resultant lysate was clarified by centrifugation at 12,000×g. For immunoprecipitation reactions cell lysates were diluted 3-fold with PBS and aliqouts (typically 180 μl) were mixed with 2-5 μl of antisera and incubated at 4° C. for 30 min. Immune complexes were then adsorbed to fixed *S. aureus* cells by the method of Kessler (40a) and were precipitated by centrifugation at 12,000×g for 30 s. The *S. aureus* cells were then washed 3 times with wash buffer (PBS, 1 percent NP-40, 0.3 percent sodium dodecyl sulfate), and the immune complexes were eluted with 20 μl of polyacrylamide gel sample buffer (62.5 mM Tris-HCl buffer, pH 6.8 containing 10 percent glycerol, 5 percent 2-mercaptoethanol, 0.01 percent bromophenol blue) at 90° C. for 3 min. After centrifugation for 30 s the supernatants were applied to 10 percent polyacrylamide slab gels according to the method of Laemmli (45).

FIG. 4A compares autoradiographs obtained with the gD12 cell line and HSV-1 infected cells: control immunoprecipitation from the gD12 cell lysate with normal rabbit serum (lane 1); immunoprecipitation of native gD grown in HEL cells (lane 2) and A549 cells (lane 3) with the monoclonal anti-gD antibody, 55-S (41); immunoprecipitation of cloned gD from the gD12 cell lysate with polyclonal rabbit antibodies (Dako Corp.) to HSV-1 (lane 4), and the monoclonal antibody, 55-S (lane 5); immunoprecipitation of cloned gD from the gD12 cells metabolically labeled with $^3$H-glucosamine with polyclonal rabbit anti-HSV-1 antibodies (lane 6).

It is seen (lanes 4 and 5) that a diffuse band of 59-60 kd was specifically precipitated from the gD12 cell line using either rabbit anti-HSV-1 antibodies or the monoclonal anti-gD antibody, 55-S, specific for the HSV-1 protein (41). This molecular weight agrees well with that reported for gD isolated from HSV-1 infected KB cells (42). It is seen that the same monoclonal antibody precipitated proteins of similar but different molecular weights from HSV-1 infected human cell lines. The major product precipitated from the A549 human lung carcinoma cell line (lane 2) was 53 kd and that precipitated from the human embryonic lung cell line (HEL) was 56 kd (lane 3). Previous studies (43) have shown that the molecular weight of HSV glycoproteins varies depending on the host cell and that these differences are due to differences in glycosylation. To determine whether the gD protein produced in CHO cells was, in fact, glycosylated, the cells were metabolically labeled with $^3$H-glucosamine. Because bands of identical molecular weights (lanes 5 and 6) were precipitated after metabolic labeling with $^{35}$-methionine or $^3$H-glucosamine, we concluded that the gD protein produced in CHO cells is glycosylated.

The human cell lines A549 (ATCC CCL 185) and HEL 299 (ATCC CCL 137) were grown to confluence in 3.5 cm tissue culture dishes and infected with HSV-1 at multiplicity of 10 pfu per cell. Virus infected cells were labeled by a method similar to that described by Cohen et al. (44). 4 hr after infection the medium was removed and the cells were washed once with fresh medium (Dulbecco's modified Eagle's medium) and once with phosphate-buffered saline (PBS). Fresh medium containing one-tenth the normal concentration of methionine was then added to the cells along with $^{35}$S-methionine (Amersham, International) to a final concentration of 75 µCi per ml of medium. The cells were grown an additional 20 hr and then harvested by treatment of washed cells with PBS containing EDTA (0.02 percent). Viral proteins were solubilized in lysis buffer consisting of PBS, 3 percent NP-40, 1 percent bovine serum albumin, $5 \times 10^{-5}$M phenylmethylsulfonyl fluoride, and 0.017 TIU/ml of apoprotinin. The resultant lysate was clarified by centrifugation at 12,000×g in a microcentrifuge. For immunoprecipitation reactions the cell or virus lysates were diluted 3-fold with phosphate buffered saline, mixed with 2-5 µl of the appropriate antiserum and incubated for 30 min at 4° C. Antibody-antigen complexes were removed from the reaction medium by the addition of 25 µl of a 10 percent solution fixed *S. aureus* (Kessler (40a)) and were precipitated by centrifugation at 12,000×g for 30 s. The *S. aureus* cells were then washed 3 times with wash buffer (PBS, 1 percent NP-40, 0.3 percent sodium dodecyl sulfate), and the cells suspended in 20 µl of polyacrylamide gel sample buffer (10 percent glycerol, 5 percent 2-mercaptoethanol, 0.0625 M in pH 6.8 Tris buffer, 0.01 percent bromophenol blue) and incubated at 90° C. for 3 min. After centrifugation (12,000× g) for 30 s the supernatants were applied to 10 percent polyacrylamide slab gels (45).

To further explore the post-translational processing of cloned gD, pulse-chase studies were conducted. FIG. 4B shows immunoprecipitation of cloned gD from gD-12 cells with rabbit anti-HSV-1 antibodies (Dako, Corp.) at various times after pulse labeling with $^{35}$S-methionine. FIG. 4B shows a pulse labelling of the gD12 cells. In these studies, cells were grown to confluence in 10 cm tissue culture dishes and labeled with $^{35}$S-methionine as described above with the exception that the labeling reaction was carried out for 15 min. on ice, the cells washed 3 times with fresh medium, and then returned to the incubator and incubated at 37° C. for various times. The reactions were terminated by washing the cells in cold phosphate-buffered saline and solubilizing the cells as described above. Proteins were immunoprecipitated at the following times after pulse labeling: lane 1, 5 min; lane 2, 15 min; lane 3, 30 min; lane 4, 60 min; lane 5, 120 min. The precursor form of gD with a molecular weight of 51 kd was specifically precipitated from the gD12 cell line 5 min after a pulse with $^{35}$S-methionine, and this precursor chased into the higher molecular weight form (59 kd) after approximately 60 min. From these studies we estimate the half-time for this post-translational event to be approximately 45 min. The precursor-product relationship between the 51 kd band and 59 kd band closely resembles that reported for virus produced gD (14,42,46,47) and the kinetics of this process are similar to those described by Cohen et al. (42). In virus infected cells the difference in molecular weights between the precursor and the product has been attributed to both N-linked and O-linked oligosaccharides (48).

Figure 5:
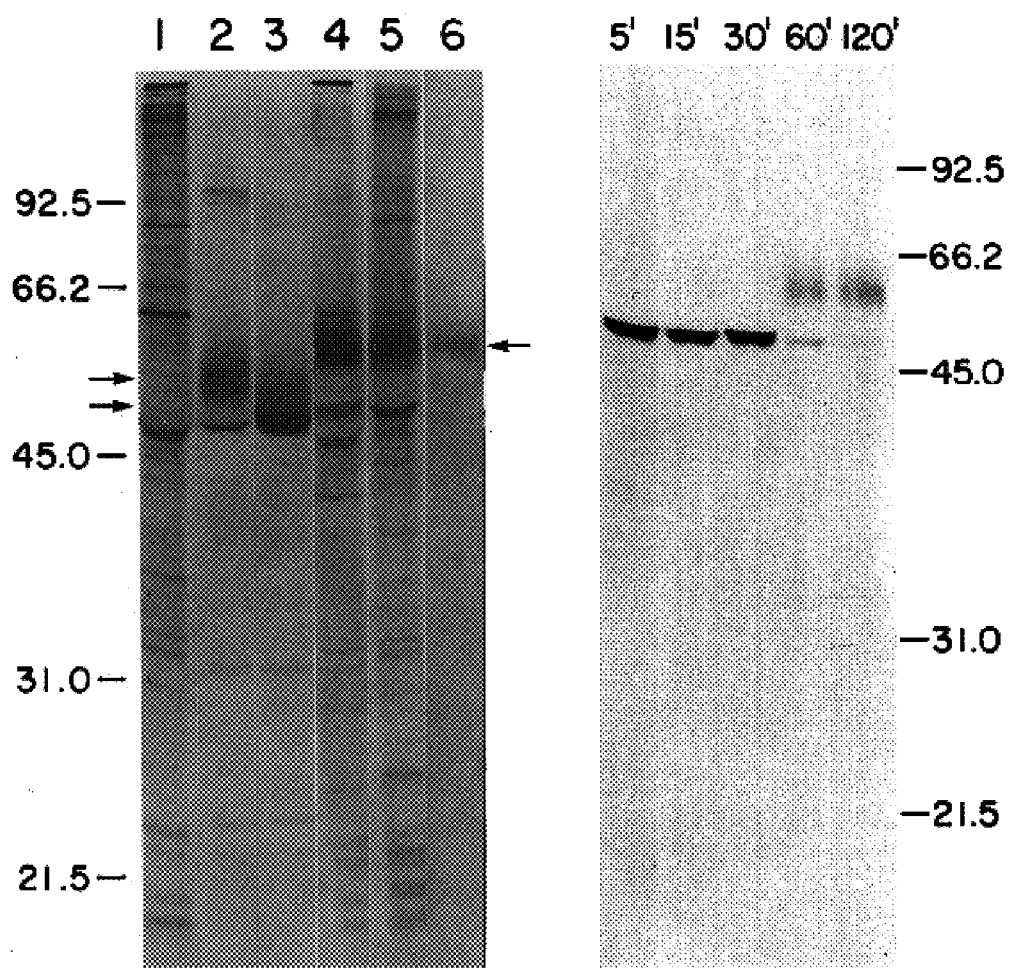
FIGS. 5A and 5B show radioimmunoprecipitations of cloned gD from the gD12 cell line hereof and native gD from HSV-1 infected human cells.

To determine whether gD was exported to the cell surface, indirect immunofluorescence studies were conducted. In these studies rabbit, mouse, and human anti-HSV antibodies were reacted with unfixed cells under conditions which do not permeable the cell membrane (49). gD12 cells and the parental CHO cells (1:1 ratio) were plated onto glass coverslips (2.2×2.2 cm) and grown until the cells were approximately 60 percent confluent. Human serum known to contain antibodies to HSV-1 (50) was diluted forty-fold with phosphate buffered saline (PBS) and 100 µl was pipetted onto washed cells and was incubated for 30 min. at room temperature in a humidified chamber. The cells were immersed 3 times in PBS to wash away unbound antibody and then were incubated with 100 µl of 20-fold diluted tetramethylrhodamine isothiocyanate-labeled goat anti-human IgG antibodies (Cappel Laboratories) for an additional 30 min. The unbound labeled antibody washed away with PBS and the cells were dehydrated in ice cold 50 percent ethanol and 100 percent ethanol and rehydrated with glycerol on a microscope slide (49). The cells were then viewed under phase-contrast and fluorescence optics in fluorescence microscope (Zeiss). FIG. 5 shows: A, gD12 and CHO cells viewed visualized with phase contrast optics; B, fluorescence image of the same cells as in A. Comparison of the phase-contrast images with the fluorescence images (FIG. 5) showed that the gD12 cells were heavily labeled, while the parental CHO cells bound little or no labeled antibody. In control experiments with normal mouse sera, normal rabbit sera, or human sera known to be negative for HSV antibodies, no specific labeling of the cells could be detected. These studies suggested that the gD was exported to the cell surface. Experiments with CHO and gD12 cells fixed prior to labeling with agents known to permeable the cell membrane (methanol or acetone) gave a different labeling pattern. In these studies we observed heavy perinuclear labeling of the gD12 cells with anti-HSV-1 antibodies, and no specific labeling of the CHO cells.

In order to determine whether gD12 cells expressed antigenic determinants relevant to human HSV-1 and HSV-2 infections, the binding of antibodies from individuals known to possess anti-HSV-1 or anti-HSV-2 antibodies (50) was examined. Radioimmunoprecipitation of lysates from metabolically labeled gD12 cells gave results comparable to those obtained with rodent anti-HSV sera (FIG. 4). Similarly, human anti-HSV-1 sera gave specific labeling of gD12 cells in an indirect immunofluorescence assay (FIG. 5) and did not label the parental CHO cell line. Taken together, the results obtained with various rodent anti-HSV-1 and HSV-2 antisera, monoclonal anti-gD antibodies and human anti-HSV antisera provide evidence that gD expressed on the surface of gD12 cells possesses a number of antigenic determinants in common with the native virus and that the structure of these determinants is not dependent on interactions with other HSV-1 proteins. The fact that one of the monoclonal antibodies tested (1-S) is known to neutralize HSV-1 in vitro (41) and in vivo (51) demonstrates that the gD produced in CHO cells possesses at least one of the neutralizing antigenic determinants in common with the native virus.

In order to have a quantitative measure of the binding of anti-HSV antibodies to gD12 cells, an enzyme-linked immunosorbtion assay (ELISA) was developed (52). In these studies gD12 cells and CHO cells were plated and chemically fixed into alternate wells of 96 well microtiter tissue culture plates. Various antisera known to possess antibodies to HSV were then serially diluted and allowed to react with the fixed cells. At the end of the assay, the absorbance in each well was measured and normal binding curves were constructed. The specific binding of antibodies to the gD12 cells was determined by subtracting the values obtained with the parental CHO cells from those obtained from the gD12 cells. Specific binding by high titer sera could be detected at dilutions of 1:10,000.

Figure 6:
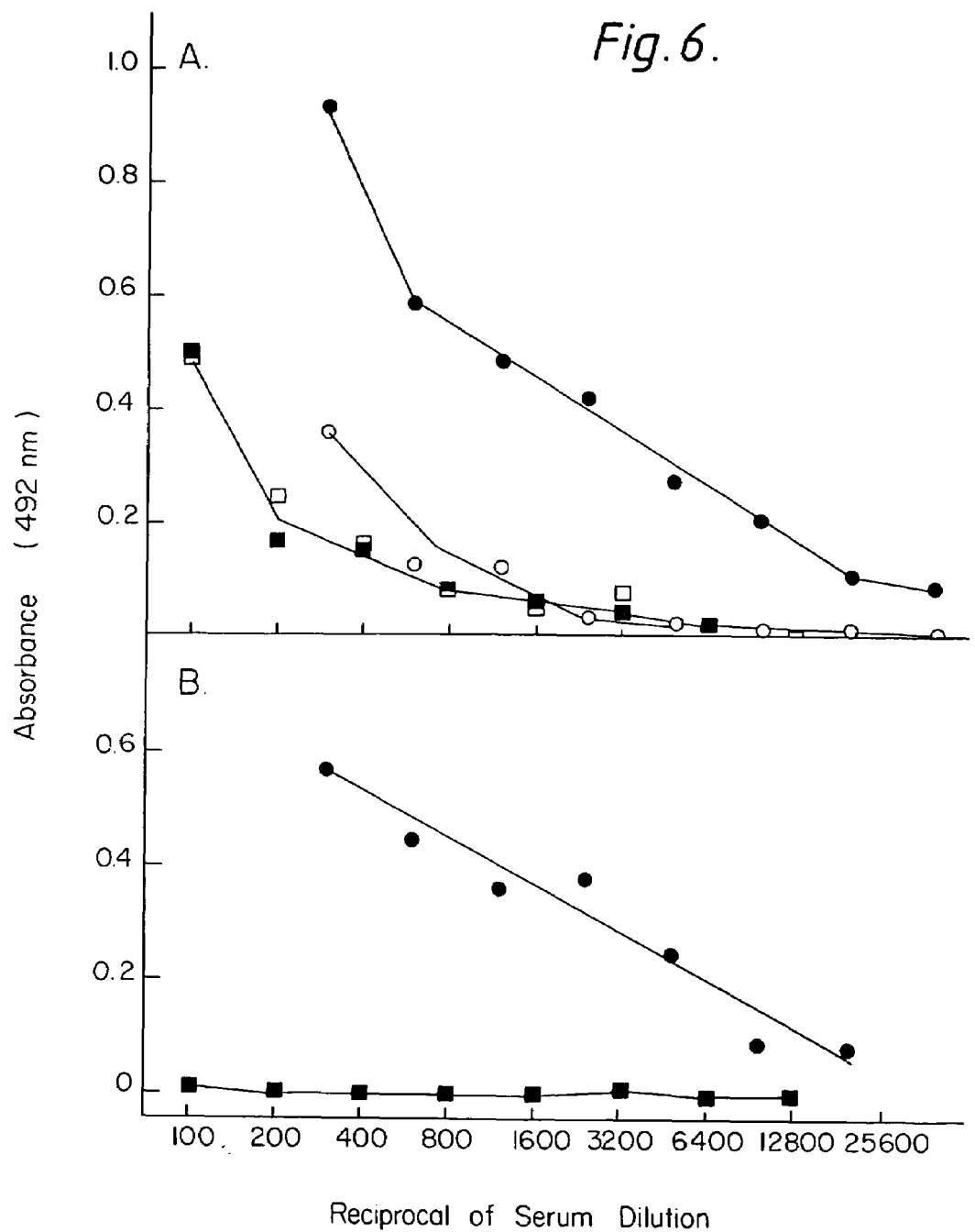
FIGS. 6A and 6B show the binding of human anti-HSV antibodies to gD12 cells and the parental CHO cell line.

We compared serum titers determined using the gD12 cell ELISA assay with anti-HSV-1 and anti-HSV-2 titers determined by conventional methods. Human sera previously titered (50) against HSV by conventional assays, i.e., inhibition of hemagglutination (IHA) or complement fixation (CF), was serially diluted into wells of microtiter plates containing either gD12 cells or the parental CHO cell line and the binding of anti-gD antibodies was monitored in an ELISA assay. gD12 cells and the parental CHO cells were seeded into alternate wells of 96 well microtiter tissue culture plates (Falcon Labware) and were grown to confluence in F12 medium (GIBCO) containing 10 percent fetal bovine serum. The cells were washed three times with phosphate-buffered saline (PBS) and then were chemically fixed with 0.0625 percent glutaraldehyde in PBS. The cells were again washed three times with PBS and stored until needed at 4° in PBS containing 1 percent bovine serum albumin, 100 mM glycine 1 mM NaN$_3$. To measure anti-gD antibody titers, the cells were washed with PBS, and serially diluted antisera was allowed to react with the fixed cells (50 μl final volume) for 1 hr at room temperature. Unbound antibody washed away and the cells were incubated with 50 μl of 1:2000 diluted goat anti-human IgG coupled to horseradish peroxidase (Tago, Inc.). The enzyme-linked antibody was allowed to react for one hour at room temperature, and the cells were then washed three times with PBS. After incubation, the peroxidase substrate, o-phenylene diamine, was added (200 μl) and the reaction was allowed to proceed for 10 min. The reaction was terminated by the addition of 2.5 M H$_2$SO$_4$ (50 μl) and the absorbance of the reaction medium from each well was determined with an automated plate-reading spectrophotometer (Titertek). In FIG. 6, the serum represented by the open and closed circles exhibited a HSV-1 CF titer of 128 and HSV-1 and HSV-2 IHA titers of 4096. The serum represented by open and closed squares exhibited a HSV-1 CF titer of <8 and HSV-1 and HSV-2 IHA titers of <8. A, closed circle and closed square indicates binding to gD12 cells; open circle and open square indicates binding to CHO cells. B, closed circle and closed square represents the specific binding to gD12 cells calculated by subtraction of the values in A. In FIG. 6 it can be seen that a serum with a high anti-HSV titer determined by conventional assays gave a high ELISA titer, while another serum with low anti-HSV titers gave no detectable binding in the gD12 ELISA.

The studies described demonstrate that stable cell lines constitutively express on their surface a transfected gene product which binds with antibodies generated by herpes virus infection.

Immunization of Mice with gD12 Cells.

Twenty female BALB/c mice (5 weeks of age) were obtained from Simonsen Laboratories (Gilroy, Calif.). The mice were divided into two groups of 10 mice each: an "experimental" group and a "control" group. Each mouse in the experimental group was injected with gD12 cells known to express HSV-1 glycoprotein D on their surface. Each mouse in the control group was injected with the parental Chinese hamster ovary cell line (CHO cells) from which the gD12 cell line was derived. For immunization of mice both types of cells were grown to confluence in 15 cm tissue culture dishes. The CHO cells were grown in Hams F12 medium (GIBCO) supplemented with 7 percent commercially dialyzed fetal bovine serum (GIBCO), penicillin (100 U/ml), and streptomycin (100 U/ml). The gD12 cells were grown in the same medium lacking glycine, hypoxanthine, and thymidine. To harvest the cells, each dish washed twice with 15 ml of phosphate buffered saline (PBS) and then treated with 15 ml of PBS containing 0.02 percent EDTA. After 15-20 min. the cells were then removed from the dish and pelleted by centrifugation for 5 min. at full speed in a clinical centrifuge (IEC model CL clinical centrifuge, rotor model 221). The supernatant was discarded and the cells were resuspended in PBS to a final concentration of 1 ml PBS per each 15 cm dish of cells. Each mouse was then injected with 0.5 ml of cell suspension (~5×10$^6$ cells) distributed as follows: 0.25 ml injected interperitoneally, and 0.25 ml injected subcutaneously in the loose skin of the back of the neck. The mice were then boosted twice with fresh cells (prepared as described above) on day 38 and day 55 after the initial immunization. Mice were bled via the tail vein on day 68 to obtain sera for in vitro neutralization studies. Mice were challenged with HSV-1 (MacIntyre strain) on day 70. The virus challenge entailed an interperitoneal injection of 2×10$^7$ pfu of virus into each mouse. The mice were scored daily for mortality and every other day for weight change and the onset of paralysis. All of the mice in the control group died within 7 days of the virus challenge, while all of the experimental mice were protected and showed no sign of infection. These studies conclude that immunization with the gD12 cells protect from a lethal HSV-1 virus challenge.

A variety of transfection schemes are possible, of course, using a variety of selectable markers. For example, mouse L cells can be usefully transfected using a mutant dhfr gene as a selectable marker. The gD gene was transfected into such cells via a vector harboring such a marker. In principle, the strategy which we have described could be applied to any situation where the expression of a membrane protein is desired.

Expression of a Truncated Form of the gD Gene

Figure 7:
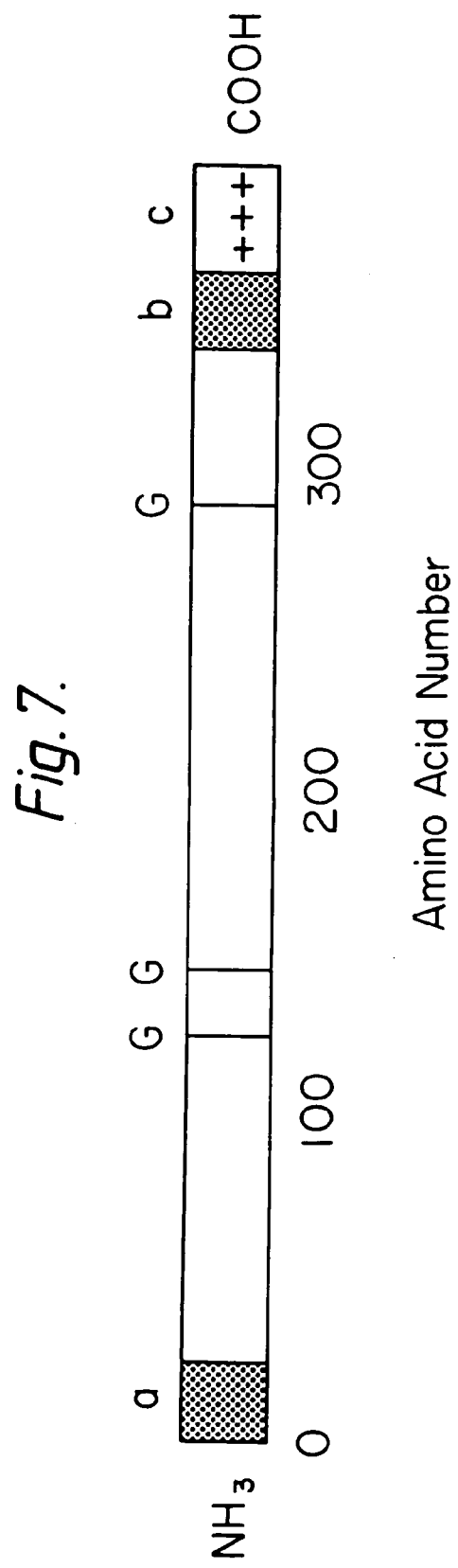
FIG. 7 is a schematic representation of HSV-1 gD protein and illustrates the locations of signal sequence and membrane-binding domain.

The foregoing description relates to the production of membrane-bound gD protein. However, as discussed above in relation to FIG. 2, analysis of the amino acid sequences of the gD protein of HSV-1 and HSV-2 identified in each case a hydrophobic/hydrophilic carboxy-terminal membrane binding domain (FIG. 7).

A Schematic Diagram of the HSV 1 Glycoprotein D (gD)

Hydrophobic (shaded) and hydrophilic (market +) regions of the protein were determined from the hydropathy analysis (31a) of the gD protein sequence derived from the gene sequence. Only those regions thought to be important for membrane localization and binding are shown. The functional domains are: a) the signal sequence (33), b) the hydrophobic transmembrane domain, and c) the charged membrane anchor. The three putative N-linked glycosylation sites are shown by the letter G. The expression plasmid consisted of the pBR322 bacterial origin of replication and ampicillin resistance gene, a cDNA insert encoding the murine dihydrofolate reductase gene under the transcriptional control of the SV40 early promoter (53) and a Hind III-Hinf 1 fragment which encodes the first 300 amino acids of gD under the transcriptional control of a second Sv40 early promoter. The Hind III site of this fragment lies 74 bp to the 5' side of the initiator methionine of the gD gene. The Hind III site of the SV-40 early region vector (36) lies 250 bp to the 3' side of the Goldberg-Hogness box of the SV40 promoter. The Hinf 1 site (blunted with Klenow DNA polymerase and 4 deoxynucleotide triphosphates) is ligated to the Hpa 1 site of the 3' nontranslated region of the hepatitis B virus surface antigen gene (36). This method is also useful for preparing a truncated HSV-2 gene. The resultant sequence creates a stop codon (TAA) immediately after amino acid 300 of the gD gene. The transcription termination and polyadenylation sites for the truncated gD gene transcript are encoded by the 3' untranslated region of the hepatitis B surface antigen gene (36).

The plasmid pgDtrunc.dhfr was constructed as follows: The 2.9 kilobase gD-containing Sac 1 fragment was isolated from the Bam HI fragment cloned from the HSV 1 genome (see above) in the plasmid pFM3 (see above) cut with Sac 1. A 1.6 kilobase Hind III-Bst N1 fragment containing the entire gD gene was subclone into Hind III-Bst N1 digested pFM42 (EPO Application No. 68693). This plasmid was then cut with Hinf 1, blunted with Klenow DNA polymerase and four deoxynucleotide triphosphates, and then subsequently cut with Hind III. The 960 base pair Hind III-blunt Hinf 1 fragment containing the truncated gD gene was isolated and ligated to Hind III-Hpa 1 digested pEHBal14. The resultant construction (pgDCos-trunc) contained the truncated gD gene with the hepatitis B surface antigen gene at its 3 prime end. A 2.3 kilobase Hind III-Bam HI fragment containing the truncated gD gene was isolated from pgD-Cos-trunc. The 2.8 kilobase fragment containing the SV 40 origin-early promoter and the pBR322 ampicillin resistance gene and bacterial origin of replication were isolated from the plasmid pEHBal 14. The 2.1 kilobase fragment containing the murine dihydrofolate reductase cDNA clone under the transcriptional control of a second SV 40 early promoter was isolated from the plasmid pE348HBVE400D22 (36). These three fragments were ligated together with T4 DNA ligase, and the resultant mixture was used to transform E. coli strain 294. Plasmid DNA from the resultant colonies was screened with Sac 2, and the correct construction pgDtrunc.dhfr (FIG. 8) was used for further transfection studies.

Plasmid pEHBal 14 was constructed by cleaving pE342ΔRI (described below), an SV40-hepatitis chimera, with Xba I, which cleaves once in the coding region of the HBV surface antigen, and sequentially removing sequences surrounding this Xba I site by using nuclease Bal31. The plasmid was ligated in the presence of the synthetic oligonucleotide 5'-AGCTGAATTC, which joins the HBV DNA with a Hind III restriction site.

Resulting plasmids were screened for an Eco RI-Hind III fragment of ~150 b.p. pEHBal 14 was sequenced, which verified that a Hind III site had been placed at a point just upstream of where the HBsAg initiation codon is normally found. This construction thus places a unique Hind III site suitable for cloning at a position where a highly expressed protein (HBsAg) initiates translation. Any putative signals necessary for high expression of a protein should be present on this 5' leader sequence.

Plasmid pE342 which expresses HBV surface antigen (also referred to as pHBs348-E) has been described by Levinson et al, EPO Publication No. 0073656, Mar. 9, 1983, which is incorporated herein by reference. (Briefly, the origin of the Simian virus SV40 was isolated by digesting SV40 DNA with Hind III, and converting the Hind III ends to EcoRI ends by the addition of a converter (AGCT-GAATTC)). This DNA was cut with Pvu II, and RI linkers added. Following digestion with Eco RI, the 348 base-pair fragment spanning the origin was isolated by polyacrylamide gel electrophoresis and electroelution, and cloned in pBR322. Expression plasmid pHBs348-E was constructed by cloning the 1986 base-pair fragment resulting from EcoRI and Bgl II digestion of HBV (Animal Virus Genetics, (Ch. 5) Acad. Press, N.Y. (1980)) (which spans the gene encoding HBsAg) into the plasmid pML (Lusky et al., Nature, 293: 79 (1981)) at the EcoRI and a Bam HI sites. (pML is a derivative of pBR322 which has a deletion eliminating sequences which are inhibitory to plasmid replication in monkey cells). The resulting plasmid (pRI-Bgl) was then linearized with Eco RI, and the 348 base-pair fragment representing the SV40 origin region was introduced into the Eco RI site of pRI-Bgl. The origin fragment can insert in either orientation. Since this fragment encodes both the early and late SV40 promoters in addition to the origin of replication, HBV genes could be expressed under the control of either promoter depending on this orientation (pHBS348-E representing HBs expressed under control of the early promoter). pE342 is modified by partially digesting with Eco RI, filling in the cleaved site using Klenow DNA polymerase I, and ligating the plasmid back together, thus removing the Eco RI site preceding the SV40 origin in pE342. The resulting plasmid is designated pE342ΔRI.

The resultant sequence creates a stop codon (TAA) immediately after amino acid 300 of the gD gene. The transcription termination and polyadenylation sites for the truncated gD gene transcript are encoded by the 3' untranslated region of the hepatitis B surface antigen gene (36).

Figure 9:
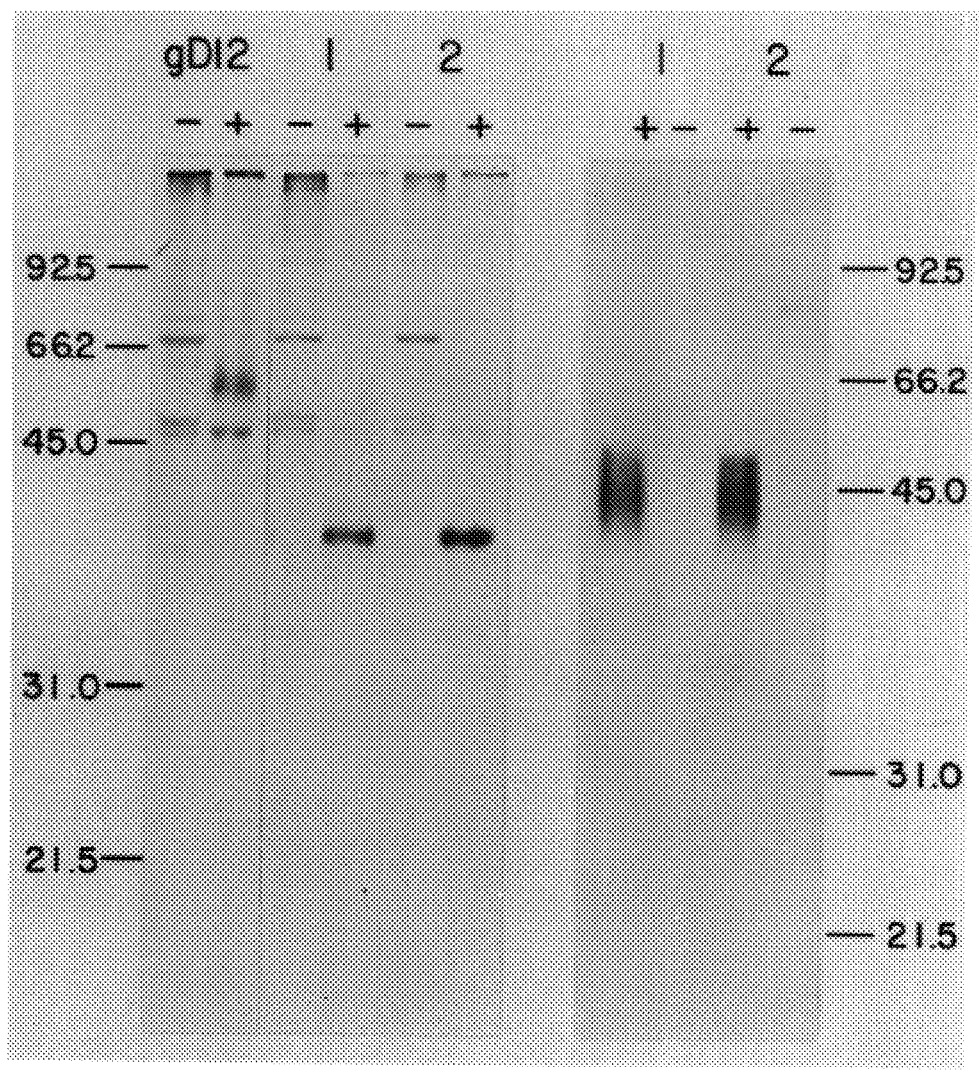
FIG. 9 shows radioimmunoprecipitations from the gD10.2 cell line hereof.

The resulting vector was transfected (40) into a dhfr⁻ CHO cell line (39), and a suitable clone gG10.2 selected which produced the truncated gD protein and secreted it into the surrounding medium. The protein was extracted from the medium and the cells were tested for immunogenic activity. FIG. 9 shows the results of immunoprecipitations of intra- and extra-cellular $^{35}$S-methionine-labelled extracts.

Radioimmunoprecipitation of cell associated- and secreted-forms of gD. Cells were grown in Ham'F12 medium (GIBCO) supplemented with 7 percent commercially dialyzed fetal bovine serum (GIBCO), penicillin (100 u/ml), and streptomycin (100 u/ml). When the cultures were approximately 80 percent confluent, the medium was removed, the cells were washed twice with phosphate buffered saline (PBS), and labeling medium (Dulbecco's modified Eagle's medium containing one-tenth the normal concentration of methionine) was added to a final concentration of 0.05 ml/cm2. $^{35}$S-methionine (SJ.204, Amersham Int.) was added to a final concentration of 50-75 uCi/ml and the cells were grown for an additional 18-20 hr. After labeling, the medium was harvested and the cells were washed twice in PBS, and removed from the culture dish by treatment with PBS containing 0.02 percent EDTA. The cells were then solubilized in lysis buffer consisting of: PBS, 3 percent NP-40, 0.1 percent bovine serum albumin, $5\times10^{-5}$ M phenylmethylsulfonyl fluoride, and 0.017 TIU/ml of apoprotinin and the resultant lysate was clarified by centrifugation at 12,000×g. For immunoprecipitation reactions cell lysates were diluted 3-fold with PBS and aliqouts (typically 180 μl)

were mixed with 2-5 µl of antisera and incubated at 4° C. for 30 min. To immunoprecipitate the secreted form of gD, 500 µl of conditioned medium was incubated with 2 µl of antisera for 30 min at 4° C. Immune complexes were then adsorbed to fixed *S. aureus* cells by the method of Kessler (40a) and were precipitated by centrifugation at 12,000×g for 30 s. The *S. aureus* cells were then washed 3 times with wash buffer (PBS, 1 percent NP-40, 0.3 percent sodium dodecyl sulfate), and the immune complexes were eluted with 20 µl of polyacrylamide gel sample buffer (62.5 mM Tris-HCl buffer, pH 6.8 containing 10 percent glycerol, 5 percent 2-mercaptoethanol, 0.01 percent bromophenol blue) at 90° C. for 3 min. After centrifugation for 30 s the supernatants were applied to 10 percent polyacrylamide slab gels according to the method of Laemmli (45). A, immunoprecipitation of full length membrane bound gD from the gD12 cell line. B, immunoprecipitation of the cell associated form of the truncated gD from lysates of two independently derived cell lines (1 and 2). C, immunoprecipitation of the truncated gD from the culture supernatants of the two cell lines shown in B. (−), indicates control rabbit antiserum; (+), indicates rabbit anti-HSV-1 antiserum (Dako Corp.).

As can be seen, evident are an intracellular form of 35,000 Daltons and a secreted and apparently glycosylated extracellular gD protein.

Preparation of Truncated gD Used for Immunization gD10.2 cells were grown to confluence in polystyrene tissue culture roller bottles (Corning 25140) in F12 medium supplemented with 7 percent commercially dialyzed fetal calf serum, 50 µg/ml streptomycin, and 0.3 µg glutamine. After reaching confluence the medium was removed and the cells were washed three times in the same medium lacking fetal calf serum and supplemented with 2 mg/ml Hepes buffer (serum free medium). The cells were then grown 3-4 days in serum free medium and the conditioned medium was then harvested and stored at ~20° C. The medium was thawed at 37° C. and centrifuged at 5000 rpm for 20 min. in a Sorvall GS-3 rotor. After centrifugation the pellet was discarded and the supernatant was concentrated in an ultra-filtration apparatus (AMICON, YM-10 membrane equipped with a YM-5 ultrafiltration membrane. The resultant preparation was concentrated approximately 150-fold relative to the starting material and contained approximately 8 mg of protein per liter. The preparation was then dialyzed extensively against phosphate buffered saline (PBS) and used for immunization without further purification.

Immunization of Mice

Each 8-week old BALB/c mouse was immunized with 36 µg of protein contained in 200 µl of an emulsion consisting of 50 percent aqueous antigen and 50 percent complete Freund's adjuvant. Each mouse was immunized at multiple intradermal and subcutaneous site as follows: 25 µl in each rear footpad, 50 µl in the tail, and 100 µl distributed among 3-5 intradermal sites along the back. Four weeks after the primary immunization the mice were boosted with 36 µg of the protein as above with the exception that the emulsion was prepared with incomplete Freund's adjuvant. For the booster immunization each mouse received 200 µl of the antigen emulsion distributed as follows: 50 µl in the tail, 150 µl distributed among 5 intradermal sites along the back. 19 days after boosting approximately 500 µl of blood was collected from each mouse by tail bleeding. The sera obtained from this bleed was used for in vitro neutralization studies (see below). 37 days after boosting the mice were used for virus challenge studies. Control mice matched to the experimentals with regard to age, sex and strain were immunized with human serum albumin (15 µg per mouse) using the same protocol as with the experimentals.

In Vitro Neutralization

Sera from eleven mice immunized with concentrated gD10.2 culture supernatant were tested for the ability to neutralize HSV-1 in vitro. Serially diluted mouse serum (2-fold dilutions: 1:8 to 1:16384) were incubated with approximately 40 pfu of HSV-1 for 1 hr. at 37° C. in Dulbecco's modified Eagle's medium (DMEM). After the serum incubation, each dilution was applied to approximately 40,000 Vero cells contained in each well of a 96 well tissue culture plate. After 3-4 days virus growth was determined by staining each well with 0.5 percent crystal violet. Wells in which virus growth occurred showed no staining. Neutralization titers were calculated by determining the highest serum dilution which prevented virus induced cell death. All of the sera tested (n=10) from mice immunized with gD10.2 supernatant material showed HSV-1 neutralization activity (range 1:16 to 1:512) and HSV-2 neutralization activity (range 1:8 to 1:16). Control mouse sera (n=8) failed to provide any neutralization. Serum obtained from a mouse immunized with HSV-1 gave a neutralizing titer of 1:32.

Virus Challenge

Eleven mice immunized with concentrated gD10.2 supernatant and 13 control mice immunized with human serum albumin were challenged with 10,000,000 pfu of HSV-1 (MacIntyre strain) by intraperitoneal injection. 14 days after the injection of virus, none of the gD10.2 immunized mice showed any indication of viral infection. In the control group, 7 of the 13 mice were dead by day 14, 3 showed severe wasting and paralysis, and 3 looked healthy. Statistical analysis (two tailed Fisher exact test) revealed that the difference between the immunized and control groups was significant at the P=0.002 level. (See Table 1).

TABLE 1

| Expt. | No of Mice | Antigen | HSV1 neut.[1] | HSV2 neut.[1] | HSV1[2,4] Paralyzed | Challenge Dead | Alive |
|---|---|---|---|---|---|---|---|
| 509C | 11 | gDtrunc[3] | 1:16-1:512 | 1:8-1:16 | 0 | 0 | 11 |
| 509D | 13 | HSA | 0 | 0 | 3 | 7 | 3 |

[1]Mouse sera were tested for HSV1 and HSV2 neutralization activity 19 days after the second secreted gD booster vaccination. Serially diluted mouse sera (1:8-1:16384) were incubated with 40 forming units of HSV1 or HSV2 for 1 hour at 37° C. Each dilution was applied to 40,000 Vero cells contained in each well of 96 well microtitre wells. After 4 days, the cells were stained with 0.5 percent crystal violet. Neutralization titres were calculated by determining the highest serum dilution which prevented virus growth.
[2]Mice were challenged by intraperitoneal injection of 1 × 10[7] plaque forming units of HSV1 (MacIntyre strain). Challenged mice were observed for a period of three weeks for HSV1 infection.
[3]Each mouse was immunized with approximately 3 micrograms of secreted gD in a 50 percent aqueous, 50 percent Freund's adjuvant solution. Mice were immunized at multiple intradermal and subcutaneous sites. Four weeks after the primary immunization, mice were boosted. Mice were challenged 19 days after the booster immunization. Control mice were immunized with an equivalent amount of human serum albumin (HSA).
[4]Significant at p = 0.002 level.

It was found that the truncated protein released into the medium from gD10.2 cells was effective to protect mice from a lethal infection from HSV-1.

Antigen Preparation for HSV-2 Virus Challenge

Amplified gD10.2.2 cells, grown in the presence of 250 nM methotrexate, were seeded into roller culture bottles (850 cm$^2$) and were cultured in Ham's F12 medium (GIBCO) supplemented with 7 percent fetal bovine serum. After the cells reached confluence (approximately 3 days), the culture medium was removed, the cells were washed three times in phosphate buffered saline (PBS) to remove serum proteins, and new "serum free" culture medium was added. The serum free medium consisted of Ham's F12 medium containing 25 mM Hepes buffer. The cells were then cultured for three days and the resultant conditioned medium was harvested and used for antigen preparation. Fresh serum-free medium was then added to the cells and the cycle of harvesting conditioned medium at three day intervals was repeated an additional one or two times until the cells died or no longer adhered to the culture surface. gD10.2.2 conditioned serum-free medium was then filtered and centrifuged at low speed to remove cellular debris, and the resultant material was then concentrated ten- to twenty-fold with an ultrafiltration device (YM-10 membrane, AMICON). The concentrated medium was then dialyzed overnight against PBS (3 changes of PBS, one liter per change). The resulting material was then assayed to determine the protein concentration and analyzed by polyacrylamide gel electrophoresis to determine protein composition and to estimate the purity of the preparation. The material prepared by this process was then used to immunize animals against HSV-2 infection as described below.

Immunization of Mice Against HSV-2 Infection

Forty female BALB/c mice were obtained from the Charles River Laboratories (Boston, Mass.) and were immunized with the secreted gD protein (gDtrunc) or human serum albumin (HSA) at 12 weeks of age. For the primary immunization against the secreted gD protein, the antigen was adjusted to a concentration of approximately 70 ug per ml in phosphate buffered saline and was emulsified with an equal volume of complete Freund's adjuvant. Each mouse was then immunized with 200 µl of this emulsion distributed as follows: 50 µl subcutaneously at a site approximately 1 cm from the base of the tail, 25 µl subcutaneously in each rear footpad, and 100 µl distributed among 3-5 intradermal sites along the back. The mice were then boosted with the same antigen one month after the primary immunization. For the booster immunization the antigen was prepared by the same procedure as with the primary immunization with the exception that incomplete Freund's adjuvant replaced complete Freund's adjuvant. For the booster immunization, 200 µl of antigen emulsion was injected into each mouse and was distributed as follows: 50 µl in the tail, 25 µl subcutaneously in the loose skin above each thigh, and 100 ul distributed among 3-5 intradermal sites along the back. The control group of mice was immunized according to the same protocol as the experimental group of mice with the exception that human serum albumin replaced the secreted gD protein as the immunogen. Serum was collected from the mice 24 days after boosting for use in in vitro neutralization studies.

HSV-2 Virus Challenge

Both experimental (secreted gD injected) and control (HSA injected) groups of mice were challenged by an intraperitoneal injection of HSV-2 (MS strain) 31 days after the booster immunization. Each mouse received 2×10$^5$ pfu of virus in 100 µl of Dulbecco's modified Eagle's medium (DMEM) containing 10 percent fetal bovine serum. LD 50 experiments revealed that this amount of virus represented 100-500 times the amount of virus required to kill 50 percent of a population of normal (uninjected) BALB/c mice. The virus injected mice were observed for a period of 3 weeks. All of the control mice (HSA injected) died within 9 days of the virus challenge. All of the mice vaccinated with the secreted gD protein survived the full three weeks and appeared normal (i.e., they did not exhibit wasting or paralysis).

TABLE 2

| Expt. | No. of Mice | Antigen | HSV1 neut.[1] | HSV2 neut.[1] | HSV1[2] Challenge Paralyzed | Dead | Alive |
|---|---|---|---|---|---|---|---|
| 579C | 15 | gDtrunc | 1:1024-1:2048 | 1:512-1:1024 | 0 | 0 | 15 |
| 579D | 25 | HSA | 0 | 0 | 0 | 25 | 0 |

[1]Mouse sera were tested for HSV1 and HSV2 neutralization activity 19 days after the second secreted gD booster vaccination. Serially diluted mouse sera (1:8-1:16384) were incubated with 40 forming units of HSV1 or HSV2 for 1 hour at 37° C. Each dilution was applied to 40,000 Vero cells contained in each well of 96 well microtitre wells. After 4 days, the cells were stained with 0.5 percent crystal violet. Neutralization titres were calculated by determining the highest serum dilution which prevented virus growth. Values indicated represent the average neutralization titers.
[2]See text above for the details of the HSV-2 challenge.

The advantages of using the truncated protein for diagnostic and vaccine applications is that, being secreted into the extracellular medium, it is contaminated with far fewer proteins than would be found in a whole-cell preparation.

It will be noted that the present invention uses a permanent cell line to produce the protein. Upon transfection the vector is incorporated into the genome of the cell line and can produce the protein without cell lysis. The cell line can thus be used for continuous production of the protein, especially in the truncated form which is secreted from the cell. For example, the cells expressing truncated protein can be continuously used in a perfusion system by constantly removing antigen-rich medium from the cells and replacing it with fresh medium.

The particular cell line used here was a CHO line deficient in dhfr production, transfected with a vector containing a dhfr marker. By exposing the cell line to methotrexate (Mtx) under suitable conditions (54) the dhfr production and hence the linked gD protein production can be amplified. Three cell lines derived by transfection of the truncated gD gene into dhfr$^-$ CHO cells were plated in parallel, labeled with $^{35}$S-methionine, and immunoprecipitated as described in FIG. 2. Lanes 1 and 2 indicate the amount of secreted gD immunoprecipitated from 500 µl of culture medium conditioned by two independently isolated cell lines before selection with methotrexate. Lane 3 indicates the amount of truncated gD immunoprecipitated from an equal volume of culture medium from a cell line (gD10.2.2) selected for growth in 250 nM methotrexate. Rabbit anti-HSV-1 antibodies (Dako Corp.) were used for the immunoprecipitations shown in lanes 1-3. Lane 4 represents a control immunoprecipitation of 500 µl of medium conditioned by the gD10.2.2 cell line with normal rabbit serum.

Figure 10:
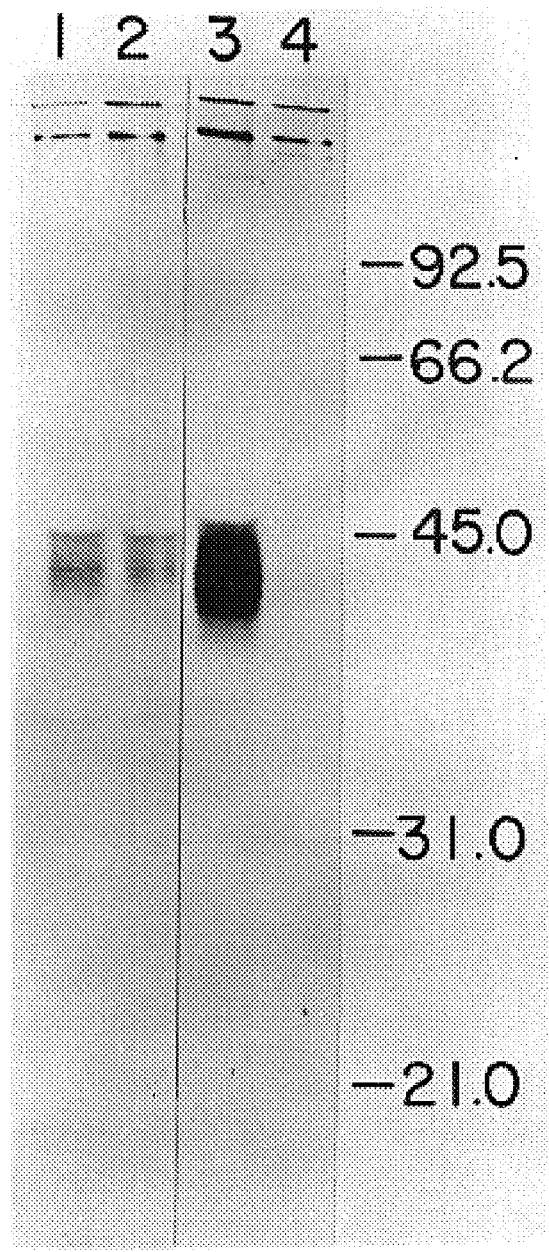
FIG. 10 shows radioimmunoprecipitations from preamplified and amplified gD10.2 cell lines.

To quantitate the relative amounts of truncated gD secreted into the culture medium by cell lines before and after selection in methotrexate, a competitive ELISA assay was performed. gD12 cells expressing a membrane-bound form of gD were plated out and fixed with glutaraldehyde to the surface of 96 well microtiter plates as previously described. Conditioned medium from various cell lines known to produce the truncated gD was serially diluted across the microtiter plate and was incubated with a fixed quantity (2 µl) of rabbit anti-HSV-1 antibody (Dako Corp) for 1 hr at 20° C. Unbound antibody and soluble truncated gD-antibody complexes were removed by washing each well 3 times with PBS. Horseradish peroxidase coupled to goat anti-rabbit IgG was then reacted with the fixed cells for 1 hr at 20° C. and unbound antibody was removed by washing 3 times with PBS. The colorometric substrate, OPD (o-phenylene diamine), was then added to each well and allowed to react with the bound horseradish peroxidase-antibody complexes for 15 min. The reaction was terminated by the addition of sulfuric acid to a final concentration of 0.25 N. The absorbance of the OPD in each well was determined with the use of an automated microtiter plate scanner (Titertek multiskan) and dilution curves were plotted. The binding of anti-HSV-1 antibodies to the parental CHO cell line was used to measure the extent of nonspecific binding at each dilution. The amount of truncated gD in each culture supernatant was inversely proportional to the amount of absorbance in each well. Open circle, binding of anti-HSV-1 antibodies to gD12 cells in the presence of medium conditioned by cells secreting truncated gD before amplification with methotrexate. Closed circle, binding of anti-HSV-1 antibodies to gD12 cells in the presence of medium from gD10.2.2 cells selected for growth in 250 nM methotrexate. Open square, binding of anti-HSV-1 antibodies to gD12 cells in the presence of 100-fold concentrated medium from unamplified cells secreting truncated gD. This procedure was carried out on the gD10.2 cell line to produce an amplified cell line gD10.2.2 which was capable of growth in 250 nM Mtx and which secreted approximately 20-fold more truncated gD into the culture medium than the parental gD10.2 cell line (see FIGS. 10 and 11).

The dhfr marker/amplification system can be used with other cells which are able to acquire and stably incorporate foreign DNA.

The success of this invention in demonstrating that a truncated form of a membrane bound protein, lacking that part of the hydrophobic-hydrophilic carboxy-terminal region responsible for binding it to the membrane, can yet be immunogenic indicates that similar results can be expected with other immunogenic membrane bound proteins, thus providing an improved source of vaccine against viruses, parasites and other pathogenic organisms.

In the foregoing example, the DNA of gD protein was truncated at residue 300 because there was a convenient restriction site there. This had the result that the carboxy-terminal hydrophobic/hydrophilic region was completely removed, as can be seen from the hydropathy plot of FIG. 2; indeed an additional preceding region was removed from residue 301 to 332 without, apparently, destroying the immunogenic character of the protein. It would seem to follow, therefore, that with this protein, and probably with other immunogenic membrane bound proteins, the extent of truncation could be considerably less if desired, so long as it has the effect of removing the membrane binding character so that the protein is secreted into the surrounding medium.

Example 2

Example 2 Relates to an HSV-2 gC Protein (Formerly Designated a gF Protein)

Cells, Virus, and DNA Isolation

HSV-2 (strain G) was grown on HEp 2 cells after infecting the cell culture at an input multiplicity of 0.1 for 3 days at 33° C. in Dulbecco's Modified Eagles Medium containing 10 percent fetal bovine serum and antibiotics. HSV-2 DNA was isolated by proteinase K digestion followed by CsCl ultracentrifugation as described (23).

DNA Manipulations

Restriction enzymes, DNA polymerase Klenow fragment, T4 DNA ligase, and T4 polynucleotide kinase were purchased from Bethesda Research Labs and were used according to the suppliers' directions.

Molecular Cloning of HSV-2 DNA Restriction Fragments

The Eco RI "P" fragment, which corresponds to approximate map position ~0.650 of the HSV-2 genome, was isolated from Eco RI digested HSV-2 DNA on 5 percent acrylamide gels. The isolated fragment was cloned into Eco RI digested pUC9 (28). This plasmid was called pUC-RIP.

The pUC-RIP subclone was then used to localize a Sac 1 fragment of the HSV-2 genome which contained the Eco RI "P" fragment. Southern blot experiments (27) revealed that a 4.9 kb fragment of HSV-2 contained the Eco RI "P" fragment. This fragment was isolated on 0.7 percent agarose gels and was cloned into a pBR322-derived plasmid which contained a unique Sac 1 site (55). This plasmid was called pBRSac1-"E". Further restriction enzyme analysis of pBRSac1-"E" demonstrated a 2.9 kb fragment with sequences homologous to the Eco RI "P" fragment which was subcloned into Sal 1 digested pUC9 as described above. This plasmid was called pgC$_2$Sal2.9.

DNA Sequence Analysis of Cloned HSV-2 DNA

The majority of DNA sequences were determined using the dideoxy nucleotide chain termination technique. Various fragments were subcloned into the replicative form of the m13 phage vectors mp7, mp8, and mp9, and the DNA sequence was determined as described previously (29). In some cases, fragments were $^{32}$P-labelled at their 5' ends with $\gamma^{32}$P-ATP and T4 polynucleotide kinase and the DNA sequence of the fragment was determined by using the chemical degradation method (56). Computer-assisted analysis of DNA and protein sequence data was performed using the HOM program (57). The hydropathy of the deduced amino acid sequences was analyzed using a width of 12 amino acids and a jump of 1 (31a).

Southern Blot Analysis of HSV-2 DNA

Restriction endonuclease digested HSV-2 DNA and plasmid DNA were fractionated on 1.5 percent agarose gels and blotted onto nitrocellulose using standard procedures. The single-stranded ends of the Sac 2 fragment, marked with a star in FIG. 12, were filled in with the Klenow fragment of DNA polymerase Sma 1, and the resultant blunt-ended fragment was ligated to Sma 1 digested m13mp7 replicative form (29) with T4 DNA ligase. The single-stranded DNA prepared from this ligation and transfection was used as a template for the synthesis of $^{32}$P-labeled single-stranded probe DNA of high specific activity (1×10$^9$ cpm/μg) using the Klenow fragment of DNA polymerase I. Hybridizations were performed using standard procedures (27,58).

Results

Molecular Cloning of the gF Coding Region of the HSV-2 Genome

The strategy adopted for the isolation of the gF gene of HSV-2 was based on the assumption that this gene was colinear with the HSV-1 gC gene. This assumption was supported by the recent finding that a 75,000 dalton glycoprotein, gF, with antigenic relatedness to HSV-1 glycoprotein C is found in HSV-2 and that the gene for this protein is approximately colinear with the HSV-1 gC gene (22d,59). In addition, the isolation of a monoclonal antibody which binds to both HSV-1 gC and HSV-2 gF further suggested that these two proteins may be homologous to each other (22f). It was thus reasoned that DNA sequence analysis of the HSV-2 genomic region which is colinear with the HSV-1 gC gene would result in the derivation of protein sequence information which would localize the HSV-2 gF gene.

The 600 basepair Eco RI "P" fragment of the HSV-2 genome has been shown to map at position ~0.650 (12). This region is approximately colinear with the known coding region of the HSV-1 gC gene which maps between approximately 0.630 and 0.640 of the HSV-1 genome (59). This fragment was isolated from an Eco RI digest of HSV-2 DNA, cloned in the plasmid pUC9 (28), and its DNA sequence was determined (29,56). Comparison of the resultant sequence with the HSV-1 gC sequence (59) revealed a remarkable degree of sequence homology between the Eco RI "P" fragment and the 3' end of the HSV-1 gC coding region. Thus, the Eco RI "P" fragment was subsequently used as a probe to isolate a Sac 1 restriction endonuclease fragment from HSV-2 genomic DNA that overlapped the Eco RI "P" fragment sufficiently to include the remainder of the HSV-2 gene which was homologous to the HSV-1 gC gene. FIG. 12 illustrates the steps taken to isolate a 2.9 kb Sal 1 fragment from the HSV-2 genome which contained the Eco RI "P" fragment and which was used for subsequent DNA sequence analysis.

DNA Sequence Analysis of the Eco RI "P" Region of the HSV-2 Genome

The 4.3 kb Sac 1 "E" fragment which was isolated from the HSV-2 genome based upon its sequence homology to the Eco RI "P" fragment, was further digested to give a 2.9 kb Sal 1 fragment which was termed pgC$_2$Sal2.9. FIG. 12 illustrates the fragments from pgC$_2$Sal2.9 which were subjected to DNA sequence analysis using either the dideoxynucleotide sequencing procedure (29) or the chemical degradation procedure (56). In addition, this figure shows the position of the Eco RI "P" fragment within pgC$_2$Sal2.9 as well as the position of a Bgl II site which corresponds to the right hand end of the Bgl II "N" fragment at position ~0.628 of the HSV-2 genome (12).

Specifically, FIG. 12 shows the cloning of pgC$_2$Sal2.9, the HSV-2 region which maps colinearly with HSV-1 gC. The region of the HSV-2 genome mapping from ~0.61-0.66 was cloned as a Sac 1 fragment (pBRSac "E") using the 600 basepair Eco RI "P" fragment as a probe. A Sal 1 subclone of pBRSac "E", pgC$_2$sal2.9, was used for DNA sequence analysis. Arrows refer to the sequenced regions, and the location of a major 479 amino acid open reading frame derived from the sequence is illustrated. Various restriction sites are illustrated, including the Eco RI sites which delineate the EcoRI "P" fragment, and the Bgl II site which is found at the right end of the Bgl II "N" fragment (map position ~0.628) (26). The Sac 2 fragment marked with a star (*) was used in Southern blotting experiments to investigate the deletion which appears in this region (see results). Other sites were used for DNA sequencing experiments. Sm; Sma 1, Sa; Sac 2, Rs; Rsa I, Bg; Bgl II, Pv; Pvu II, RI; Eco RI.

FIG. 13 illustrates the DNA sequence obtained from pgC$_2$Sal2.9 compared with the DNA sequence of the HSV-1 gC region (59). The HSV-1 gC region (HSV-1) and the sequence obtained from pgC$_2$Sal2.9 (HSV-2) were compared using the HOM program (57). Because various deletions were utilized to maximize sequence overlap, all positions, including spaces, have been numbered for clarity. Stars are placed over non-matching nucleotides. The underlined "A" residue at position 43 of the HSV-1 sequence is the approximate transcriptional start site of the gC mRNA (59).

"TATA" 1 and "TATA" 2 are the probable transcriptional control regions for the HSV-1 gC mRNA and the 730 base mRNA, respectively (59,60). The inserted T residue at position 1728 of the HSV-1 sequence was discovered by resequencing this region (M. Jackson, unpublished) and was found to introduce an in-phase stop codon at positions 1735-1737 which was homologous to the stop codon for the HSV-2 major open reading frame. The position of the 730 base mRNA initiation codon of HSV-1 is shown at position 2032-2034, as is the position of a second HSV-2 initiation codon at position 1975-1977.

Referring again to FIG. 13, the illustrated derived sequence of HSV-2 was compared with the DNA sequence of the gC gene region of HSV-1 (59) which showed an overall sequence homology between these two fragments was approximately 68 percent. However, certain regions of the sequence showed either a much higher or lower degree of sequence homology than others. For example, the sequences between positions 0 and 570 of the HSV-1 and HSV-2 sequences showed only 51 percent homology, while the region between position 570 and 1740 showed a much higher degree of sequence homology (80 percent). An additional highly homologous region (70 percent) was also found at the end of the two sequences from position 1975 to position 2419. In addition to the nucleotide sequence changes, the two genomes showed various deletions or insertions when compared to each other. The most notable was an 81 basepair region found at position 346-426 of the HSV-1 gC sequence which is missing from the HSV-2 genome. From this overall sequence comparison it appeared that there was a high degree of sequence homology between the HSV-1 gC region and the HSV-2 region sequenced here.

Frink et al. (59) have found that the 5' end of the 2,520 base mRNA encoding HSV-1 gC maps to the underlined A residue at position 43 of FIG. 13. In addition, they pointed out an AT-rich "TATA" box (60) sequence approximately 22 basepairs 5' to this residue. Comparison of the two sequences shown in FIG. 13 shows that the HSV-1 and HSV-2 sequences both contained the identical sequence, CGGGTATAAA, in this region. This sequence is identical to that reported previously by Whitton et al. (61), which is found to occur at the "TATA" box regions in many of the HSV-1 and HSV-2 sequences determined thus far. This conserved sequence is also followed by a G-rich region in both virus genomes. In addition to this putative transcriptional-control region, a second "TATA" box was found in both sequences at position 1845-1849 of FIG. 13. This second "TATA" box has been hypothesized to control the transcription of a 730 base mRNA in the HSV-1 genome (59). Both HSV-1 and HSV-2 contain this sequence surrounded by GC-rich flanking sequences, including a CGGGCG sequence which is similar to the CGGG sequence preceding the first "TATA" box. In addition, both genomes encode open reading frames 3' to these second "TATA" boxes, which will be discussed below.

In order to determine if the 81 basepair deletion described above was actually found in the HSV-2 genome or if it was an artifact of cloning or sequencing, Southern blot analysis of the HSV-2 genomic DNA and the cloned HSV-2 DNA was performed. A $^{32}$P-labeled probe was prepared from a Sac II fragment (see fragment in FIG. 12) which spans the region missing the 81 nucleotides. If the HSV-2 genomic DNA is missing the 81 basepair region, then a Sma 1-Bgl II fragment spanning this region will be 576 basepairs, a Sma 1 fragment will be 662 basepairs, and a Sac II fragment will be 195 basepairs.

FIG. 14 illustrates Southern blot analysis of HSV-2 genomic DNA and pgC$_2$Sal2.9 DNA. The region spanning the 81 basepair region missing in the HSV-2 sequence shown in FIG. 13 (HSV-2 positions 346-426) was analyzed using the Sac II fragment marked with a star in FIG. 12 which overlaps the delete region. Lanes 1-3 are restriction digests of HSV-2 genomic DNA, and lanes 4-6 are restriction enzyme digests of pgC$_2$Sal2.9. The digested DNAs were electrophoresed on 1.5 percent agarose gels, denatured, blotted onto nitrocellulose, and probed with the $^{32}$P-labeled Sac II fragment. (The arrow shows the position of the 564 base pair Hind III fragment of phage λ DNA.) Lanes 1,6; Sma 1+Bgl II: lanes 2,5; Sma 1: Lanes 3,4; Sac II.

The results shown in FIG. 14 demonstrate that the predicted restriction sites surrounded the region missing the 81 basepairs in both the HSV-2 genomic DNA and the cloned HSV-2 DNA. In addition, the HSV-2 genomic fragments and the cloned fragments comigrated exactly, demonstrating that the deletion is not an artifact of cloning or sequencing.

Analysis of the Major Open Reading Frame within the HSV-2 2.9 kb Sal 1 Fragment

Analysis of the potential coding sequences within the 2.9 kb Sal 1 DNA fragment of HSV-2 revealed an open reading frame of 479 amino acids which began with the methionine encoded at position 199-201 of the HSV-2 sequence shown in FIG. 13 and ended at the TAA termination codon at position 1735-1737 of the HSV-2 sequence in this figure. As can be seen from FIG. 13, both the HSV-1 gC protein and the HSV-2 open reading frame initiate at approximately the same position in the two sequences, relative to the "TATA" box homologies. In addition, while it initially appeared that the HSV-2 open reading frame found in this region terminated 12 codons before the HSV-1 gC gene, resequencing of the carboxy-terminal region of the gC gene sequence (M. Jackson, unpublished) of HSV-1 strain F revealed that the sequence reported by Frink et al. (59) was missing a thymidine nucleotide after position 1727 and that insertion of this residue resulted in a translated HSV-1 gC protein terminating at the same place as the HSV-2 open reading frame (1735-1737 of FIG. 13). Thus, when taking the various deletions and insertions into account, as illustrated in FIG. 13, the HSV-1 gC gene and the HSV-2 open reading frame show a very high degree of overlap.

FIG. 15 illustrates translation of the HSV-2 large open reading frame and comparison with the HSV-1 gC amino acid sequence. The single letter amino acid symbols were used. HSV-1 gC refers to the HSV-1 gC sequence, and HSV-2 gF refers to the HSV-2 open reading frame sequence. The proteins were compared using the HOM program, which maximized homologies by inserting gaps where necessary (57). Stars are placed over non-homologous amino acids. Putative N-linked glycosylation sites (NXS or NXT) (62) are shaded, and cysteine residues (C) are boxed. Only amino acids, and not spaces are numbered. 15B illustrates translation of the second HSV-2 open reading frame and comparison with the HSV-1730 base mRNA protein. 730 ORF HSV-2 is the incomplete amino acid sequence of the second HSV-2 open reading frame from positions 1975-2406 of the HSV-2 sequence shown in FIG. 13. 730 ORF HSV-1 is the amino acid sequence derived for the protein encoded by the 730 base mRNA of HSV-1 (59). Conserved amino acid changes, with respect to charge, are marked (C) and nonconserved changes, with respect to charge, are marked (N) in both FIGS. 4A and 4B.

FIG. 15 illustrates the high degree of sequence homology between the HSV-1 gC gene and the 479 amino acid HSV-2 open reading frame. The first 19 amino acids contain approximately 80 percent sequence homology with the changes in the first 25 amino acids being all conservative with respect to charge. From residue 124 of HSV-1 gC (residue 90 of the HSV-2 sequence) to the end of both proteins there is about 74 percent sequence homology with 75 percent of the amino acid changes being conservative with respect to charge. Five putative N-linked glycosylation sites (NXS or NXT (62)) are conserved between the two proteins, and all 7 cysteine residues are located in homologous positions relative to the C-terminus. In addition to the overall conservation of sequences in the carboxy-terminal three-fourths of the proteins, there are also large regions of contiguous amino acid sequence homology up to 20 residues in length (i.e., position 385-405 of the HSV-1 sequence and 352-372 of the HSV-2 sequence). It may be concluded from this sequence comparison that the open reading frame in this region of the HSV-2 genome encodes a protein which is homologous to HSV-1 gC.

While the HSV-2 protein encoded in this region shows a remarkable degree of sequence homology to the HSV-1 gC sequence, there are several notable differences between the two sequences. The most striking difference is a deletion of 27 amino acids in the HSV-2 sequence which are found in the HSV-1 gC sequence from residues 50-76 (FIG. 15) and which corresponds to the 81 basepair deletion described above. In addition to this large deletion, both sequences show minor deletions of one or two amino acids. All of these deletions are found in the amino-terminal regions of the proteins. In addition to these deletions, there are a large number of amino acid changes in the amino-terminal region of the proteins which are clustered between residues 29-123 of the HSV-1 gC sequence (residues 31-90 of the HSV-2 sequence). Only 30 percent of the amino acids in this region are homologous, with much of this homology due to conserved proline residues. 43 percent of the amino acid substitutions found in this region are non-conservative with respect to charge. The only other regions which showed such a large number of changes are a carboxy-terminal hydrophobic domain (residues 476-496 of the HSV-1 sequence and 443-463 of the HSV-2 sequence) where the proteins are 55 percent homologous but where all the changes are conserved, uncharged, hydrophobic amino acids and the carboxy-termini of the proteins where the sequences are only 25 percent homologous, but where the overall amino acid composition is similar (residues 500-512 of the HSV-1 sequence and 467-479 of the HSV-2 sequence). While five of the putative N-linked glycosylation sites are conserved between the two proteins, the HSV-1 gC sequence contains two more sites than the HSV-2 sequence (9 versus 7 total). The HSV-1 gC sequence contains 2 N-linked glycosylation sites in the 27 amino acids deleted from the HSV-2 sequence, and an overlapping pair of sites between residues 109 and 112 of FIG. 15. The HSV-2 sequence contains two N-linked glycosylation sites not found in the HSV-1 sequence, one of which is proximal to the amino terminus.

In order to more fully examine the possible structural homologies between the HSV-1 and HSV-2 sequences, hydropathy analysis was performed (31a). FIG. 6 illustrates hydropathy analysis of the HSV-1 gC protein and the HSV-2 major open reading frame protein. The hydropathy of each protein was determined using the program of Hopp and Woods (31a). Hydrophobic regions are above the midline and hydrophilic regions are below the midline. Stretches of 12 amino acids were analyzed, and the average hydropathy was calculated. Putative asparagine-linked glycosylation sites (62) are marked (0). gC-1: HSV-1 gC protein hydropathy. gC-2 (gF): HSV-2 major open reading frame protein hydropathy.

FIG. 16 shows that both proteins exhibited an extraordinary degree of structural homology based on the hydrophilic and hydrophobic properties of the amino acid sequences. Each show an N-terminal hydrophobic domain followed by a stretch of hydrophilic amino acids which contain either 6 of 9 total (HSV-1) or 3 of 7 total (HSV-2) putative N-linked glycosylation sites. The peaks and valleys which follow this hydrophilic region are very similar in both proteins, including the hydrophilic domain containing the final N-linked glycosylation site. The carboxy-termini of both proteins shows a very hydrophobic 20 residue region followed by a hydrophilic carboxy-terminus. The 27 contiguous amino acids found exclusively in the HSV-1 gC protein appear to encode a relatively hydrophilic region between residues 50-76 (FIG. 16). In conclusion, this analysis reveals that the hydropathic features of both the HSV-1 gC and the HSV-2 protein are very similar and that the least conserved aminoterminal regions of the proteins are found in hydrophilic regions which have the potential to be highly glycosylated.

Analysis of the Second HSV-2 Open Reading Frame

Translation of the final 431 basepairs of the HSV-2 sequence shown in FIG. 2 (residues 1975-2406) revealed a second open reading frame of 105 amino acids. Although the sequence information reported here is insufficient to contain the entire HSV-2 second open reading frame, comparison of this sequence with the open reading frame encoded by the 730 base mRNA of HSV-1 reported by Frink et al. (10) also revealed a high degree of sequence homology. As can be seen in FIG. 4b, the two sequences showed 75 percent sequence homology in the overlapping regions, with about 90 percent of the amino acid changes being conservative with respect to charge. The major difference between the two sequences was a 19 amino acid N-terminal region which was found in the HSV-2, but not HSV-1 sequence. Thus, although the function of the protein encoded in this region is unknown, the proteins from HSV-1 and HSV-2 show a considerable degree of sequence homology.

Discussion

The above results demonstrate that the HSV-2 genome encodes a colinearly mapping homologue of the HSV-1 glycoprotein C. The colinearity of the sequences found here is strengthened by the finding of a sequence 3' of the HSV-2 major open reading frame which apparently encodes a homologue of the HSV-1 730 base pair mRNA (10). Previous mapping of the HSV-2 gF gene (33), together with the properties described here for the major open reading frame in this region of the HSV-2 genome including several potential N-linked glycosylation sites and an apparent amino-terminal signal sequence (5) as well as a putative carboxy-terminal transmembrane domain (28) allow the conclusion that the HSV-2 protein described here is the glycoprotein, gF. In addition, the size of the translated HSV-2 protein (~52,000 daltons) is similar to that reported for the endoglycosidase H-treated, native size for HSV-2 gF (54,000 daltons) (22d). Finally, the large extent of amino acid sequence homology as well as the conservation of several potential N-linked glycosylation sites and of all 7 cysteine residues indicates structural homology between HSV-1 gC and HSV-2 gF. These results, then, strongly suggest that the HSV-1 gC protein and the HSV-2 gF protein are homologous to each other.

These results help explain previous results which demonstrated that the HSV-2 gF and HSV-1 gC proteins were mainly type-specific, but that they did have type-common determinants (17,22d,22f,43). Since several previous studies (17,18,43) demonstrated that these proteins induced predominantly type-specific antibodies, it is reasonable that the most antigenic regions of the proteins are found within the more divergent N-terminal sequences which follow the putative hydrophobic signal sequences. The hydrophilic nature of the divergent regions, along with their high content of potential N-linked glycosylation sites (62), suggests that these regions would be located on the surface of the protein. Exposure of these divergent sequences to the outside of the proteins may be responsible for the generation of type-specific antibodies directed against these divergent epitopes. However, type-common antibodies could likely also be generated by the more highly conserved carboxy-terminal three-fourths of the proteins, since hydrophilic regions conserved between gC and gF could be exposed to the outside of the proteins and may be, in one case, glycosylated (residues 363-366 of HSV-1 gC and 330-332 of HSV-2 gF). Thus, HSV-1 gC and HSV-2 gF share both type-specific and type-common determinants, but it appears that the type-specific determinants are more antigenic.

Although an explanation of the type-specific and type-common determinants of gC and gF is not known, it is possible that the proteins have at least two functions, one of which is important for the viability of both viruses, the type common domain, and one of which is specific for each virus type, the type-specific domain. While the function(s) of gC and gF is at present unknown, and while viable gC minus mutants of HSV-1 have been isolated in vitro (65), it is not clear that either gC or gF are indispensable to the viruses during in vivo infection of the human host and the establishment of latency. It is possible that at least some of the biological differences between HSV-1 and HSV-2, including predilection for site of infection and virulence, may be due to the marked structural differences between the amino-terminal regions of gC and gF. It may be concluded, even in the absence of any functional knowledge of these proteins, that different selective pressures must be operating on the divergent and conserved domains of gC and gF.

Previous sequence comparison of the gD genes of HSV-1 and HSV-2 (58) demonstrated that the amino-terminal signal sequence (63) and the carboxy-terminal transmembrane domain (64) were able to tolerate a large number of mutations as long as the substituted amino acids were hydrophobic. The gC and gF sequence comparison demonstrates a similar finding in the carboxy-terminal, putative transmembrane domain (64) from residues 476-496 of gC and 443-463 of gF. The large number of heterologous hydrophobic substitutions in this region suggests that, as in gD, any amino acid which is lipid-soluble can be tolerated in this region. In contrast to gD, however, the amino-terminal signal sequences of gC and gF are highly homologous in the first 19 residues. Thus, either this region has an important conserved function other than direction of the glycoproteins into the rough endoplasmic reticulum (5), or there may be an overlapping gene or other functional sequence in this region of the genome which must be conserved (66).

Although insufficient HSV-2 sequence is presented here for a complete comparison, the region 5' to the start of HSV-1 gC mRNA transcription shows an identical CGGG-TATAA sequence in both the HSV-1 and HSV-2 genomes. In addition, both sequences are followed by a G-rich region immediately preceding the start of transcription. Thus, as was previously found for the gD genes of HSV-1 and HSV-2, upstream sequence homologies exist between the two virus types which suggest the possibility that these regions are involved in transcriptional regulation of these genes. Interestingly, the second "TATA" box homology found in both virus genomes, which probably controls transcription of the 730 base mRNA (59,60), also shows a relatively high degree of sequence homology in HSV-1 and HSV-2. These "TATA" boxes are preceded by CG-rich sequences, which are similar, but not identical, to those preceding the first "TATA" regions shown in FIG. 13, and they are both followed by a 14 basepair region showing ~80 percent sequence homology. The entire region of homology surrounding this region is only 33 basepairs with an overall sequence homology of ~75 percent. If this region is involved in transcriptional regulation of the 730 base mRNA, then it appears that a relatively short sequence may be sufficient for recognition by transcriptional regulatory elements.

The results demonstrate that the HSV-1 gC and HSV-2 gF glycoproteins are highly homologous, and that they encode type-common and type-specific domains. Since the two proteins do show significant sequence homology, and since they apparently map colinearly, we favor the proposal of Zezulak and Spear (22d) to rename HSV-2 gF as HSV-2 gC or gC-2. In addition, the sequencing data reported here opens the way for a functional analysis of the gC-1 and gC-2 proteins by the interchange of various type-specific regions between the two proteins in vitro and expression of the chimaeric sequences in mammalian cells (67) or by reincorporation of these regions back into the virus (68).

It is believed that the cloned gC-2 glycoproteins may be expressed and formed into a vaccine in a manner analogous to that set forth in Example 1.

It is further believed that a vaccine which includes a mixture of such recombinant gC and gD glycoproteins would be significantly more effective as a vaccine against HSV-1 and HSV-2 than one based upon either glycoprotein alone.

The references grouped in the following bibliography and respectively cited parenthetically by letter and number in the foregoing text, are hereby incorporated by reference.

BIBLIOGRAPHY

1. Emtage, et al., *Nature* 283, 171 (1980); Davis, et al., *Proc. Natl. Acad. Sci.* (*USA*) 78, 5376 (1981); Weiland, et al., *Nature* 292, 851 (1981).
2. Kupper, et al. *Nature* 289, 555 (1981); Kleid, et al. *Science* 214, 1125 (1981).
3. Charnay, et al., *Nucleic Acids Research* 7, 335 (1979); Valenzuela, et al., *Nature* 298, 347 (1982).
4. Rose, et al., *Proc. Natl. Acad. Sci.* (*USA*) 78, 6670 (1981).
5. Yelverton, et al., *Science* 219, 614 (1983).
6. Watson, et al., *Science* 218, 381 (1982).
7. Gething, et al., *Nature* 293, 620 (1981); Liu, et al., *DNA* 1, 213 (1982); Goodenow, et al., *Science* 215, 677 (1982); Goodenow, et al., *Nature* 300, 231 (1982); Crowley, et al., *Molec. and Cell. Biol.* 3, 44 (1983).
8. Rose, et al., *Cell* 30, 753 (1982).
9. Spear P. G., (1980), Herpesviruses, p 709-750, in H. A. Blough and J. M. Tiffaney (ed)., *Cell Membranes and Viral Envelopes*, Vol. 2., Academic Press, Inc., New York.
10. Balachandran, et al., *J. Virol.* 44, 344 (1982).
11. Norrild, *Curr. Top. Microbiol Immunol.* 90, 67 (1980).
12. Roizman, *Cell* 16, 481 (1979).
13. Baucke, et al., *J. Virol.* 32, 779 (1979).
14. Cohen, et al., *J. Virol.* 27, 172.
15. Eberle, et al., *J. Virol.* 36, 665 (1980).
16. Norrild, et al., *J. Virol.* 26, 712 (1978).
17. Powell, et al., *Nature* 249, 360 (1974).
18. Eberle, et al., *Infect. Immun.* 31, 1062 (1981).
19. Pereira, et al., *Infect. Immun.* 29, 724.
20. Sim, C., et al., *J. Gen. Virol.* 19, 217 (1973).
21. Showalter, et al., *Infect. Immun.* 34, 684 (1981).
22a. Eisenberg, et al., *J. Virol.* 41, 1099.
22b. Balachandran, et al., *J. Virol.* 39, 438 (1981).
22c. Para, et al., *J. Virol.* 41, 137 (1982).
22d. Zezulak, et al., *J. Virol.* 47, 553 (1983).
22f. Zweig, et al., *J. Virol.* 47, 185 (1983).
23. Anderson, et al., *J. Virol.* 30, 805 (1979).
24. Lee, et al., *J. Virol.* 43, 41 (1982).
25. Murray, et al., *Mol. Genet.* 150, 53 (1977).
26. Benton, et al., *Science* 196, 180 (1977).
27. Southern, *J. Mol. Biol.* 98, 503 (1975).
28. Vieira, et al., *Gene* 19, 259 (1982).
29. Messing, et al., *Nuc. Acid. Res.* 9, 309 (1981).
30. Sanger, et al., *Proc. Natl. Acad. Sci.* (*USA*) 74, 5436 (1977).
31. *Atlas of Protein Sequence and Structure V.*5, Supplement 2, 1976, M. O. Dayhoff, ed., The Biochemical Research Foundation, Spring, Md., p. 311.
31a. Hopp, et al., *Proc. Natl. Acad. Sci.* (*USA*) 78, 3824 (1981).
32. Watson, et al., *Nucl. Acid. Res.* 11, 1507 (1983).
33. Blobel, *Proc. Natl. Acad. Sci.* (*USA*) 77, 1746 (1980).
34. Rose, et al., *Proc. Natl. Acad. Sci.* (*USA*) 77, 3884 (1980).
35. Ruyechan, et al., *J. Virol.* 29, 677 (1979); Roizman, *Cell* 26, 481 (1979).
36. Simonsen, et al., *Proc. Natl. Acad. Sci.* (*USA*) 80, 2495 (1983).
37. Lusky, et al., *Nature* 293, 79 (1981).
38. Nunberg, et al., *Cell* 19, 355 (1980).
39. Urlaub, et al., *Proc. Natl. Acad. Sci.* (*USA*) 77, 4216 (1980).
40. Graham, et al., *Virol.* 52, 456, (1973).
40a. Kessler, *J. Immuno.* 115, 1617 (1975).
41. Showalter, et al., *Infect. and Immun.* 34, 684 (1981); Monoclonal anti-gD antibodies, 1-S and 55-S were kindly provided by Dr. Martin Zweig of the Laboratory of Molecular Oncology, National Cancer Institute, Frederick, Md. 21701.
42. Cohen, et al., *J. Virol.* 36, 429 (1980).
43. Pereira, et al., *Proc. Natl. Acad. Sci.* (*USA*) 78, 5202 (1981).
44. Cohen, et al., *J. Virol.* 27, 172 (1978).
45. Laemmli, *Nature* 227, 680 (1970).
46. Honess, et al., *J. Virol.* 16, 1308 (1975).
47. Spear, *J. Virol.* 17, 991 (1976).
48. Campadelli-Fiume, et al., *J. Virol.* 43, 1061 (1982); Johnson, et al., *Cell* 32, 987 (1983); Cohen, et al., *J. Virol.* 46, 679 (1983).
49. Bloch, *J. Cell. Biol.* 82, 629 (1979).
50. Human herpetic serum titered against HSV-1 and HSV-2 by inhibition of hemagglutination and complement fixation assays was kindly provided by Dr. John A. Stewart of the Centers for Disease Control, Atlanta, Ga.
51. Rector, et al., *Infect. and Immun.* 38, 168 (1982).
52. Kennett, in *Monoclonal Antibodies*, K. Kerrett, T. McKearn, and B. Bechtel, eds. (Plenum Press, N.Y., 1980), pp. 376-377.
53. Fiers, et al., *Nature* 273, 113 (1978); Gluzman, *Cell* 23, 275 (1981).
54. Lee, et al., *Nature* 294, 228 (1981); Kaufman, et al., *Mol. and Cell. Biol.* 2, 1304 (1983); Kaufman, et al., *J. Mol. Biol.* 159, 601 (1982).
55. Kleid, et al., *Science* 214, 1125 (1981).

56. Maxam, et al., *Methods Enzymol.* 65, 499 (1980).
57. Dayhoff, M., Ed. Atlas of Protein Sequence and Structure, Vol. 5, Supplement 2, National Biochemical Research Foundation, Silver Spring, Md., p. 311 (1976).
58. Lasky, et al., *DNA*, in press (1984).
59. Frink, et al., *J. Virol.* 45, 634 (1983).
60. McKnight, et al., *Science* 217, 316 (1982).
61. Whitton, et al., *Nucl. Acids Res.* 18, 6271 (1983).
62. Hubbard, et al., *Ann. Rev. Biochem.* 50, 555 (1981).
63. Blobel, *Proc. Natl. Acad. Sci. USA* 77, 1491 (1980).
64. Sabatini, et al., *J. Cell. Biol.* 92, 1 (1982).
65. Cassai, et al., *Intervirology* 6, 212 (1975).
66. Hall, et al., *J. Virol.* 43, 594 (1982).

What is claimed is:

1. An immunogenic composition comprising a truncated, membrane-free derivative of a polypeptide comprising a membrane-binding domain and antigenic determinants capable of raising neutralizing antibodies against in vivo challenge by a pathogen, wherein said derivative:
   (a) is devoid of the membrane-binding domain whereby the derivative is free of membrane, and
   (b) has exposed antigenic determinants capable of raising neutralizing antibodies against in vivo challenge by the pathogen.

2. An immunogenic composition according to claim 1 wherein the derivative is a derivative of a herpes glycoprotein.

3. An immunogenic composition according to claim 2 wherein the derivative is a derivative of a glycoprotein of herpes simplex virus type 1 or type 2, and the pathogen is herpes simplex type 1 and/or type 2.

4. An immunogenic composition according to claim 2 wherein said derivative is produced in a stable eukaryotic cell line.

5. An immunogenic composition according to claim 4 wherein said cell line is a mammalian cell line.

6. An immunogenic composition according to claim 2 wherein the derivative is a derivative of glycoprotein D.

7. An immunogenic composition according to claim 2 wherein the derivative is a derivative of glycoprotein C.

8. An immunogenic composition according to claim 2 wherein the derivative is a derivative of glycoprotein B.

9. A method of producing an immunogenic composition according to any one of claims 1, 6, 7, or 8, said method comprising preparing a nucleic acid encoding said derivative, incorporating said nucleic acid into an expression vector, introducing said vector into a host cell, and collecting the derivative as a secretion product.

10. A method according to claim 9 wherein the host cell is a stable eukaryotic cell line.

11. A method according to claim 10 wherein the host cell is a mammalian cell line.

12. A method according to claim 10 wherein the cell line is deficient in the production of dhfr and the vector contains a dhfr selectable marker.

13. A method according to claim 9 wherein the derivative is a derivative of glycoprotein D of herpes simplex virus type 1 or type 2.

14. A method according to claim 13 wherein the derivative comprises the first 300 amino acid residues of the glycoprotein D.

15. An immunogenic composition according to claim 2 wherein said immunogenic composition comprises a mixture of glycoproteins or glycoprotein derivatives.

16. An immunogenic composition according to claim 15 wherein said mixture comprises glycoprotein C or a derivative thereof and glycoprotein D or a derivative thereof.

17. An immunogenic composition according to claim 15 wherein said mixture comprises glycoprotein D or a derivative thereof.

18. An immunogenic composition according to claim 17 wherein said mixture further comprises glycoprotein B or a derivative thereof.

19. An immunogenic composition according to claim 6 wherein said derivative comprises the first 300 residues of glycoprotein D.

20. A method according to claim 9 wherein the derivative is a derivative of glycoprotein C of herpes simplex virus type 1 or type 2.

21. A method according to claim 9 wherein the derivative is a derivative of glycoprotein B of herpes simplex virus type 1 or type 2.

22. A nucleic acid encoding a truncated, membrane-free derivative of a polypeptide comprising a membrane-binding domain and antigenic determinants capable of raising neutralizing antibodies against in vivo challenge by a pathogen, wherein said derivative:
   (a) is devoid of the membrane-binding domain whereby the derivative is free of membrane, and
   (b) has exposed antigenic determinants capable of raising neutralizing antibodies against in vivo challenge by the pathogen.

23. The nucleic acid of claim 22 wherein the derivative is a derivative of a herpes glycoprotein.

24. The nucleic acid of claim 23 wherein the derivative is a derivative of a glycoprotein of a herpes simplex virus type 1 or type 2, and the pathogen is herpes simplex type 1 and/or type 2.

25. An expression vector comprising a nucleic acid according to claim 22.

26. A stable host cell comprising an expression vector according to claim 25.

27. A host cell according to claim 26 wherein the host cell is a eukaryotic cell.

28. A host cell according to claim 27 wherein the host cell is a mammalian host cell.

29. A method of producing a truncated, membrane-free derivative of a polypeptide comprising a membrane-binding domain and antigenic determinants capable of raising neutralizing antibodies against in vivo challenge by a pathogen, said method comprising:
   (a) culturing the host cell of claim 26; and
   (b) recovering the derivative from the culture.

30. An immunogenic composition comprising a truncated, membrane-free derivative of a polypeptide comprising a membrane-binding domain and antigenic determinants capable of raising neutralizing antibodies against in vivo challenge by a pathogen, wherein said derivative:
   (a) is devoid of the membrane-binding domain whereby the derivative is free of membrane, and
   (b) has exposed antigenic determinants capable of raising neutralizing antibodies against in vivo challenge by the pathogen, wherein the pathogen is a virus.

31. An immunogenic composition comprising a truncated, membrane-free derivative of a polypeptide comprising a membrane-binding domain and antigenic determinants capable of raising neutralizing antibodies against in vivo challenge by a pathogen, wherein said derivative:
   (a) is devoid of the membrane-binding domain whereby the derivative is free of membrane, and
   (b) has exposed antigenic determinants capable of raising neutralizing antibodies against in vivo challenge by the pathogen, wherein said pathogen is a virus selected from the group consisting of herpes virus, influenza virus, foot and mouth disease virus, hepatitis virus, vesicular stomatitis virus and rabies virus.

* * * * *